(12) United States Patent
Barrett et al.

(10) Patent No.: US 11,769,598 B2
(45) Date of Patent: Sep. 26, 2023

(54) PRE-EMPTIVE ASTHMA RISK NOTIFICATIONS BASED ON MEDICAMENT DEVICE MONITORING

(71) Applicant: Reciprocal Labs Corporation, Madison, WI (US)

(72) Inventors: Meredith A. Barrett, Redwood City, CA (US); Mike Lohmeier, Sun Prairie, WI (US); Shannon M. Hamilton, Berkeley, CA (US); Michael J. Tuffli, Kentfield, CA (US); Dmitry Stupakov, Cupertino, CA (US); Christopher Hogg, San Francisco, CA (US); John David Van Sickle, Oregon, WI (US); Gregory F. Tracy, Madison, WI (US); Mark William Sehmer, Stoughton, WI (US); Robert Austin Lee, San Francisco, CA (US)

(73) Assignee: Reciprocal Labs Corporation, Madison, WI (US)

( * ) Notice: Subject to any disclaimer, the term of this patent is extended or adjusted under 35 U.S.C. 154(b) by 0 days.

(21) Appl. No.: 17/049,553

(22) PCT Filed: May 20, 2019

(86) PCT No.: PCT/US2019/033190
§ 371 (c)(1),
(2) Date: Oct. 21, 2020

(87) PCT Pub. No.: WO2019/226576
PCT Pub. Date: Nov. 28, 2019

(65) Prior Publication Data
US 2021/0082582 A1    Mar. 18, 2021

Related U.S. Application Data

(60) Provisional application No. 62/674,594, filed on May 21, 2018.

(51) Int. Cl.
*G16H 50/80* (2018.01)
*G16H 20/17* (2018.01)
(Continued)

(52) U.S. Cl.
CPC ............ *G16H 50/80* (2018.01); *A61B 5/1112* (2013.01); *A61B 5/7275* (2013.01);
(Continued)

(58) Field of Classification Search
CPC ........ G16H 50/80; G16H 20/17; G16H 40/67; G16H 10/60; G16H 50/30; G16H 50/70;
(Continued)

(56) References Cited

U.S. PATENT DOCUMENTS

2009/0194104 A1    8/2009   Van Sickle et al.
2009/0265186 A1   10/2009   Tarassenko et al.
(Continued)

FOREIGN PATENT DOCUMENTS

JP     2011-092418 A    7/2014
JP     2015-291617 A   12/2015
(Continued)

OTHER PUBLICATIONS

PCT International Search Report and Written Opinion for PCT/US2019/033190, dated Aug. 2, 2019, 17 Pages.
(Continued)

*Primary Examiner* — Michael Tomaszewski
*Assistant Examiner* — Rachael Sojin Stone
(74) *Attorney, Agent, or Firm* — McDermott Will & Emery LLP

(57) ABSTRACT

This description provides risk notifications for a geographic region to inform patients and effect behavior changes to prevent rescue events and exacerbations from occurring. A risk analysis for a geographic region is based on data gathered from a population of patients who may experience
(Continued)

respiratory events within the geographic region. Rescue medication events, environmental conditions relevant to the rescue medication events, and other contextually relevant information are detected by sensors associated with a population of patients' medicament device/s and are collected from other sources, respectively, to provide a basis to determine a risk score. This data is analyzed to determine the severity of the risk of a respiratory event occurring within a geographical region and accordingly sending a notification to patients within that geographical region.

21 Claims, 16 Drawing Sheets

(51) Int. Cl.
```
G16H 40/67      (2018.01)
G16H 10/60      (2018.01)
G16H 50/30      (2018.01)
G16H 50/70      (2018.01)
G16H 50/20      (2018.01)
A61M 15/00      (2006.01)
G01W 1/00       (2006.01)
A61B 5/11       (2006.01)
A61B 5/00       (2006.01)
A61M 16/00      (2006.01)
```
(52) U.S. Cl.
CPC .............. *A61B 5/7282* (2013.01); *A61B 5/74* (2013.01); *A61M 15/00* (2013.01); *G01W 1/00* (2013.01); *G16H 10/60* (2018.01); *G16H 20/17* (2018.01); *G16H 40/67* (2018.01); *G16H 50/20* (2018.01); *G16H 50/30* (2018.01); *G16H 50/70* (2018.01); *A61B 2560/0242* (2013.01); *A61M 15/0051* (2014.02); *A61M 2016/0015* (2013.01); *A61M 2202/064* (2013.01); *A61M 2205/3306* (2013.01); *A61M 2205/502* (2013.01); *A61M 2205/52* (2013.01); *A61M 2205/8206* (2013.01)

(58) Field of Classification Search
CPC ..... G16H 50/20; A61B 5/1112; A61B 5/7275; A61B 5/7282; A61B 5/74; A61B 2560/0242; A61M 15/00; A61M 15/0051; A61M 2016/0015; A61M 2202/064; A61M 2205/3306; A61M 2205/502; A61M 2205/52; A61M 2205/8206; G01W 1/00
USPC .............................................................. 705/3
See application file for complete search history.

(56) References Cited

U.S. PATENT DOCUMENTS

| | | | |
|---|---|---|---|
| 2016/0314256 A1* | 10/2016 | Su | G16H 20/13 |
| 2017/0109493 A1 | 4/2017 | Hogg et al. | |
| 2017/0140125 A1* | 5/2017 | Hogg | A61M 15/009 |
| 2022/0384002 A1* | 12/2022 | Choi | G16H 10/60 |

FOREIGN PATENT DOCUMENTS

| | | |
|---|---|---|
| WO | 2007052108 A1 | 5/2007 |
| WO | 2009-532072 A | 9/2009 |
| WO | 2015-0178907 A1 | 11/2015 |
| WO | 20170148876 A1 | 9/2017 |

OTHER PUBLICATIONS

JPO—Japanese Reasons for Rejections dated Jul. 3, 2023 for the corresponding Japanese Appln. No. 2020-565393, 8 pages.

* cited by examiner

| Results from V1 Model | | | | | | |
|---|---|---|---|---|---|---|
| | >20% | >30% | >40% | >50% | >60% | >70% |
| % "1s" | 26% | 26% | 25% | 23% | 22% | 20% |
| AUC Score | 0.97 | 0.97 | 0.97 | 0.963 | 0.940 | 0.939 |
| Accuracy | 0.91 | 0.91 | 0.91 | 0.89 | 0.87 | 0.85 |
| Sensitivity (NPV) | 0.90 | 0.90 | 0.90 | 0.90 | 0.91 | 0.90 |
| Specificity (PPV) | 0.91 | 0.91 | 0.91 | 0.89 | 0.85 | 0.84 |

*FIG. 7B*

| XGBoost Example: Model Outputs | |
|---|---|
| AUC Score | .64 |
| Accuracy | .60 |
| Sensitivity (NPV) | .60 |
| Specificity | .60 |

FIG. 7C

PRE-EMPTIVE ASTHMA RISK NOTIFICATIONS BASED ON MEDICAMENT DEVICE MONITORING

CROSS-REFERENCE TO RELATED APPLICATION

This application is the National Stage of International Application No. PCT/US2019/033190, filed May 20, 2019, which claims the benefit of U.S. Provisional Application No. 62/674,594, filed on May 21, 2018 which are hereby incorporated by reference in their entirety.

BACKGROUND

Field of Art

The disclosure relates generally to attachments for inhalers for treating respiratory diseases, and also to geography-based respiratory disease predictive models.

Description of the Related Art

Asthma remains a significant and costly public health problem. Worldwide, the World Health Organization estimates the population with asthma may be 300 million, and predicts that it will rise to 400 million by 2025. In the United States, asthma affects 1 in 12 individuals in the U.S. and prevalence is on the rise, leading to more than $82 billion per year in direct and indirect costs.

Despite the development of new medications, rates of hospitalizations and emergency room visits have not declined. Each year in the United States the disease causes approximately 2 million emergency department visits, 500,000 hospitalizations, and 5,000 deaths. In addition, asthma is responsible for an estimated 15 million missed days of school, and 12 million days of work. Total annual costs to US health insurers and employers are greater than $18 billion.

The majority of these exacerbations could be prevented with currently available treatments, however, only 1 in 5 asthmatics has the disease under control. Newly revised national guidelines urge doctors to more closely monitor whether treatment is controlling everyday symptoms and improving quality of life. Physicians, however, have few available tools to assess how well their patients are doing day-to-day. An increasing number of physicians have begun to use periodic, written questionnaires (such as the Asthma Control Test) to monitor patients and determine their level of control. These instruments require patients to accurately recall and report the frequency of symptoms, inhaler usage, and activity level and restriction over some period of time (usually two to four weeks). As a result, these questionnaires are subject to error introduced by biases (recall), different interpretations of symptoms, and behaviors (non-adherence), and only provide information at the time they are used.

More generally, medicament devices such as inhalers allow patients to manage respiratory symptoms such as constricted airflow. Many respiratory disease patients, such as sufferers of asthma, COPD, and cystic fibrosis, have symptoms that are related to environmental triggers and factors such as air quality, weather, land use, and the like. A patient being aware of which environmental triggers and factors affect their symptoms allows the patient to better manage their symptoms and reduce the chances for needing emergency medical care. However, a particular patient or group of patients may have sensitivities to multiple triggers and factors. Knowing which of dozens, hundreds, or more triggers and factors a patient is sensitive to and monitoring those triggers and factors for use in managing symptoms is a complex task and not currently feasible for many patients and providers.

SUMMARY

An analytics system is a unified platform for treating, monitoring, and managing rescue events resulting from asthma or other respiratory diseases such as COPD. Using asthma as an example, the analytics system tracks asthma rescue medication events occurring within a geographic region by receiving event notifications from sensors attached to a medicament device (e.g., inhaler) used by a population of patients who have authorized the analytics system to help manage their asthma. The sensors, when attached to or incorporated in a metered dose inhaler or other medicament device, record the geographical location, time, and date of the rescue usage event, and communicate that information to the analytics system. The analytics system analyzes the received events (both the most recent and previously received events) in real time or near-real time, and delivers a risk assessment and information to guide and manage the disease in the form of a notification to patients, caregivers, healthcare providers and members of a general public.

The risk score for the geographic region is determined using a combination of parameters including a record of rescue events received from the population of patients and environmental conditions relating to atmospheric, weather, air quality and built environment conditions for that geographic region. The relationship between these parameters and risk assessment generated for the geographic region is embodied in a machine learning model. The model, and system more generally, is capable of receiving input values for the parameters and categorizing a region's risk score to provide a risk assessment with accurate and medically relevant treatment options for patients within the geographic region to mitigate the risk.

By ingesting information about the timing, frequency, and location of the usage of the medication along with other contextually relevant parameter information, the analytics system helps prevent the occurrence of future asthma rescue usage events by suggesting immediately applicable changes in behavior in advance of those predicted events. This facilitates better management of an asthma treatment by the patient and their health care provider, and improve recognition of specific locations that precipitate rescue events so that the patient may avoid or accommodate these locations in the future.

Information describing a risk analysis for a geographic region allows patients suffering from respiratory diseases to make informed lifestyle choices regarding different geographical regions. For example, when searching for real estate, the ability to eliminate geographic regions with a high risk of respiratory symptoms allows patients to make informed decisions to improve their health. Similarly, when traveling, prior knowledge of a risk for a region allows patients to prepare the necessary precautions. As a result, a risk analysis for a geographic region provides patients, caregivers, providers and members of the public with anticipatory knowledge necessary for them to reduce their risk of respiratory events wherever their location may be.

According to an embodiment, a method for determining a risk of respiratory-related rescue events for a geographical region includes accessing a set of historical rescue inhaler usage events for a population of patients. Each event is previously received from a client device or attachment associated with a rescue inhaler unit or from the rescue inhaler unit that provided a rescue medication to one of the patients within the geographical region as part of each event. The method also includes determining a region-specific baseline risk threshold based on the set of events. In response to a triggering condition, the method includes accessing a set of parameter values for a model predicting asthma risk for the region and accessing a set of input values. Also in response to a triggering condition, the method includes inputting the parameter values, input values, and a baseline risk threshold into a function to determine the risk score for the region. In response to a triggering condition, the method includes sending a notification with details of the risk score to at least one of the client devices.

In one or more embodiments, the method also includes receiving a history of rescue inhaler usage events from a client device, attachment, or rescue inhaler unit.

In one or more embodiments, the threshold is determined with respect to a prior period which includes events from a window of time preceding the current time, and also a comparison across similar time periods such as monthly or seasonally across years.

In one or more embodiments, the threshold is determined as a percentage of a sum of the events within the prior period.

In one or more embodiments, the threshold is periodically determined.

In one or more embodiments, the triggering condition includes a threshold change in a physical location of the client device.

In one or more embodiments, the triggering condition includes a periodic conclusion of a time interval.

In one or more embodiments, the triggering condition includes a threshold change in the input value of at least one of a plurality of parameters.

In one or more embodiments, the parameter values are determined using a machine learned model.

In one or more embodiments, the risk score is a numerical value representing a likelihood that the patient will exceed the threshold that day.

In one or more embodiments, the parameters include at least one contextual data parameter.

In one or more embodiments, the parameters include one or more of the following: at least one current region parameter, further comprising a current latitude and longitude coordinate of the client device, a current location, a current date, a difference in number of controller puffs taken and prescribed for the patient, and a count of rescue puffs taken for the rescue event.

In one or more embodiments, the parameters include one or more of the following: at least one air pollutant parameter, further comprising but not limited to: concentration measurements of ozone, nitrogen dioxide, sulfur dioxide, carbon monoxide, carbon dioxide, particulate matter, 2.5 micrometers or less, particulate matter, 1 micrometer or less, other air pollutants, and the air quality index.

In one or more embodiments, the parameters include one or more of the following: at least one weather parameter, further comprising but not limited to: temperature, humidity, wind speed, wind direction, station pressure, precipitation, thunderstorms, and visibility.

In one or more embodiments, the risk notification is presented at a first time that is different from a second time when the risk threshold is determined.

In one or more embodiments, the risk notification comprises informational content regarding the triggering condition.

In one or more embodiments, the risk notification comprises informational content regarding at least one of the following: the events, the baseline risk threshold, and a risk categorization based on the risk score.

In one or more embodiments, the risk notification further comprises informational content regarding the rescue event, wherein the informational content further comprises a subset of parameters responsible for a change in risk categorization compared to a previous time period.

In one or more embodiments, the risk notification further comprises informational content regarding the rescue event, wherein the informational content further comprises a recommendation regarding how to prevent further rescue inhaler events wherein the recommendation is based on the subset of parameters responsible for the change in risk categorization.

BRIEF DESCRIPTION OF DRAWINGS

FIGS. 7A-7F are diagrams characterizing and analyzing the data used for testing the asthma risk analysis, according to one embodiment.

The figures depict various embodiments of the presented invention for purposes of illustration only. One skilled in the art will readily recognize from the following discussion that alternative embodiments of the structures and methods illustrated herein may be employed without departing from the principles described herein.

DETAILED DESCRIPTION

I. System Environment

Figure 1:
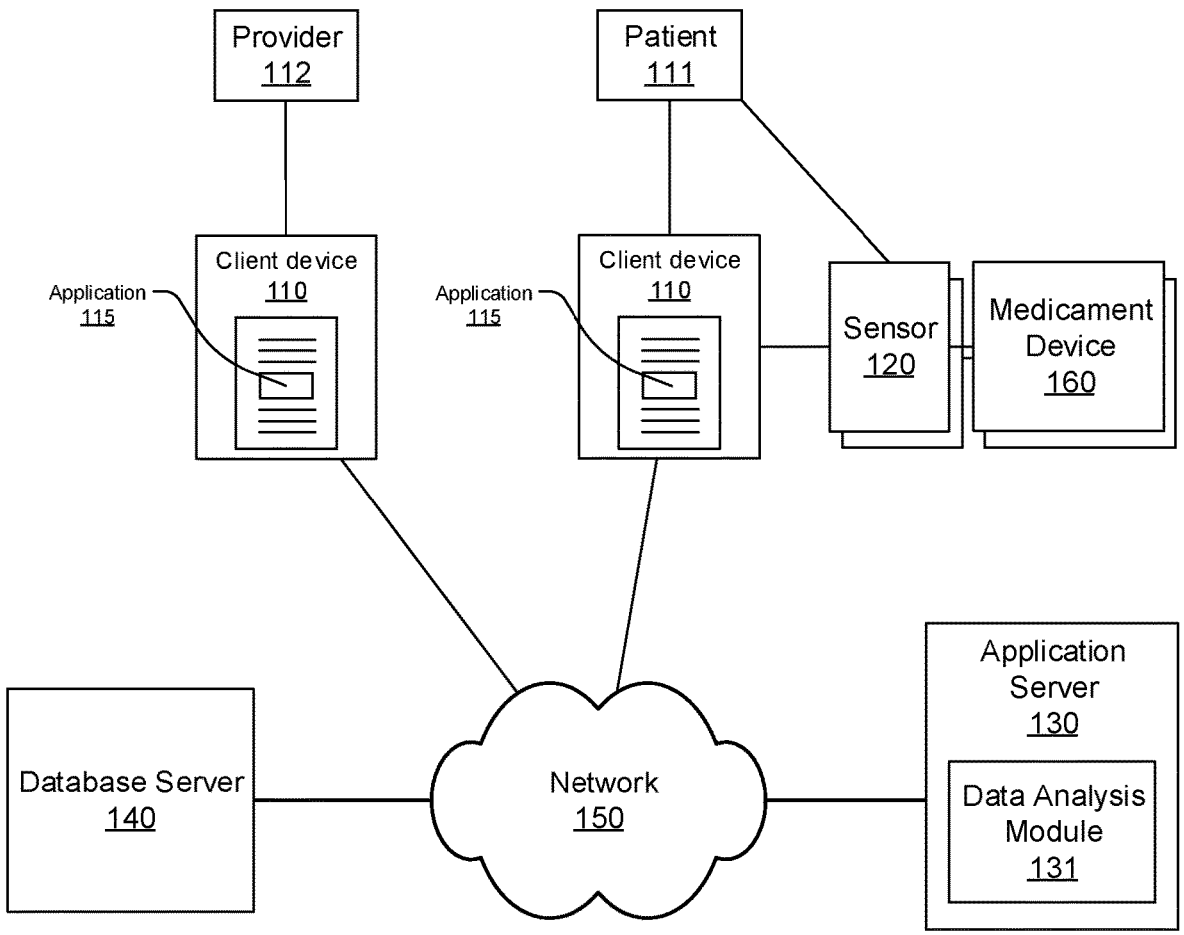
FIG. 1 shows an analytics system for monitoring accurate, real-time medicament device usage, performing analytics on that data, and providing asthma rescue event risk notifications, according to one embodiment.

FIG. 1 shows an analytics system 100 for monitoring accurate, real-time medicament device events, performing analytics on that data, and providing asthma rescue event risk notifications, according to one embodiment.

The analytics system includes client computing devices 110, a medicament device sensor 120, a medicament device 160, an application server 130, database server 140, and a network 150. Although FIG. 1 illustrates only a single instance of most of the components of the analytics system 100, in practice more than one of each component may be present, and additional or fewer components may be used.

I.A. Client Device and Application

The client devices 110, at the behest of their users, interact with the analytics system 100 via the network 150. For purposes of explanation and clarity it is useful to identify at least two different types of users. A patient 111 is a user burdened with asthma who makes use of the analytics system 100 at least in part to obtain personalized asthma rescue event risk notifications provided by the server 130 and asthma management notifications created by their health care provider 112. Such notifications can be provided in exchange for the user's permission to allow the analytics system 100 to monitor the patient's 111 medicament device 160 usage. As will be explained below, medication events are detected by a sensor 120 associated with the medicament device 160 and the user's client device 100, which in turn reports to the application server 130, which in turn can initiate a process to generate risk notifications which are provided to the user through the client device 110.

Another type of user is a healthcare provider 112 who, again with the patient's 111 express permission, also receives notifications regarding a patient's asthma management, as well as aggregated asthma community rescue event data and derived statistics regarding asthma events and other associated data. Other types of users are also contemplated, such as parents/guardians of patients 111 who may also want to receive notifications in the event that their own client devices 110 are distinct from that of their children.

The client device 110 is a computer system. An example physical implementation is described more completely below with respect to FIG. 2. The client device 110 is configured to wirelessly communicate with the analytics system 100 via network 150. With network 150 access, the client device 110 transmits to system 100 the user's geographical location and the time of a rescue medication event, as well as information describing the event as received from the associated medicament device sensor 120 (referred to throughout as "sensor 120").

Regarding user location and event times, the client device 110 may determine the geographical location and time of a rescue event through use of information about the cellular or wireless network 150 to which it is connected. For example, the current geographical location of the client device 110 may be determined by directly querying the software stack providing the network 150 connection. Alternatively, the geographical location information may be obtained by pinging an external web service (not shown in FIG. 1) made accessible via network 150. The time of an event can be provided by the sensor 120 as part of the event data or added to event data by querying an appropriate software routine available as part of the client device's native operating system.

In addition to communicating with the application server 130, client devices 110 connected wirelessly to the analytics system 100 may also exchange information with other connected client devices 110. For example, through a client software application 115, a healthcare provider 112 may receive a risk exacerbation notification describing a recent rescue event about a patient 111, then in response send a recommendation to the patient 111 for post-asthma rescue event treatment. Similarly, through application 115 patients 111 may communicate with their health care providers 112 and other patients 111.

Application 115 provides a user interface (herein referred to as a "dashboard") that is displayed on a screen of the client device 110 and allows a user to input commands to control the operation of the application 115. The dashboard is the mechanism by which healthcare providers 112 and patients 111 access the COPD analytics system 100. For example, the dashboard allows patients 111 and providers 112 to interact with each other, receive asthma rescue event risk notifications, exchange messages about treatment, provide and receive additional event and non-event data, and so on. Application 115 may be coded as a web page, series of web pages, or content otherwise coded to render within an internet browser. Application 115 may also be coded as a proprietary application configured to operate on the native operating system of the client device 110. The dashboard is more completely described below in conjunction with FIG. 3.

In addition to providing the dashboard, application 115 may also perform some data processing on asthma rescue event data locally using the resources of client device 110 before sending the processed data through the network 150. Event data sent through the network 110 is received by the application server 130 where it is analyzed and processed for storage and retrieval in conjunction with database server 140. The application server 130 may direct retrieval and storage request to the database system 130 as required by the client application 115.

The client device 110 communicates with the sensor 120 using a network adapter and either a wired or wireless communication protocol, an example of which is the Bluetooth Low Energy (BTLE) protocol. BTLE is a short-ranged, low-powered, protocol standard that transmits data wirelessly over radio links in short range wireless networks. After the sensor 120 and client device 110 have been paired with each other using a BTLE passkey, the sensor 120 automatically synchronizes and communicate information relating to medicament device usage with the client device 110. If the sensor 120 hasn't been paired with a client device 110 prior to a rescue medication event, the information is stored locally until such a pairing occurs. Upon pairing, the sensor 120 communicates any stored event records to the client device 110. In other implementations, other types of wireless connections are used (e.g., infrared or 802.11).

Although client devices 110 and medicament devices 160 are described above as being separate physical devices (such as smart phones and inhalers, respectively), in the future it is contemplated the medicament devices 160 may include not only sensors 120 integrated into a single housing with the device 160, but also aspects of the client device 110. For example, a medicament device 160 may include an audio-visual interface including a display or other lighting elements as well as speakers for presenting visual audible information. In such an implementation the medicament device 160 itself may present the contents of notifications provided by the server 130 directly, in place of or in addition to presenting them through the client devices 110.

I.B. Medicament Device and Sensor

The medicament device 160 is a medical device used to deliver medication to the lungs of a user experiencing constricted respiratory airflow. Medicament devices (e.g. inhalers) are typically portable and small enough to be carried by hand for ease of accessibility when treating respiratory attacks. In one embodiment, medicine is delivered in aerosol form through a medicament device 160 such as a metered dose inhaler. Metered dose inhalers included a pressured propellant canister of aerosol medicine, a metering valve for delivering a regulated medicine dosage amount, and a plastic holder that holds the pressurized canister and also forms a mouthpiece for delivery of the medicine. In another embodiment, medicine is delivered in dry powder form through a medicament device 160 such as a dry powder inhaler. Dry powder inhalers may have Cartesian ovular shaped bodies that house wheel and gear mechanisms enabling a user to index through a strip of dry powder medication. The bodies of dry powder inhalers also include a manifold and a mouthpiece to deliver dry powder to the user. Examples of controller medications that are dispensed by a controller medicament device 160 include beclomethasone, budesonide, and fluticasone as well as combinations of those medications with a long-acting bronchodilator such as salmeterol or formoterol. Examples of rescue medications that are dispensed by a rescue medicament device 160 include albuterol, salbutamol, levalbuterol, metaproterenol, and terbutaline.

Each patient may be associated with more than one medicament device 160. For example, the patient may have a rescue medicament device 160 that dispenses rescue medication, and a controller medicament device 160 that dispenses controller medication. Similarly, each patient may be associated with more than one sensor 120, each chosen to operate with one of the patient's medicament devices 160.

Generally, a sensor 120 is a physical device that monitors the usage of the medicament dispenser 160. The sensor 120 is either removably attachable to the medicament dispenser without impeding the operation of the medication dispenser, or the sensor 120 is an integrated component that is a native part of the medicament dispenser 160 as made available by its manufacturer.

The sensor 120 includes its own network adapter (not shown) that communicates with the client device 110 either through a wired connection, or more typically through a wireless radio frequency connection. In one embodiment, the network adapter is a Bluetooth Low Energy (BTLE) wireless transmitter, however in other embodiments other types of wireless communication may be used (e.g., infrared, 802.11).

The sensor 120 may also be configured to communicate more directly with the application server 130. For example, if the network adapter of the sensor 120 is configured to communicate via a wireless standard such as 802.11 or LTE, the adapter may exchange data with a wireless access point such as a wireless router, which may in turn communicate with the application server 130 without necessarily involving the client device 110 in every exchange of data. These two methods of communicating are not mutually exclusive, and the sensor 120 may be configured to communicate with both the client device 110 and the application server 130, for example using redundant transmission to ensure event data arrives at the application server 130 or to provide information directly to the client device 110 while the application server 130 is determining what notification to provide in response to an event.

As introduced above, the sensor 120 captures data about usage of the medicament device 160. Specifically, each sensor 120 captures the time and geographical location of the rescue medication event, that is, usages of the rescue medicament device 160, by the patient 111. Each sensor 120 transmits the event data in real-time or as soon as a network connection is achieved, automatically without input from the patient 111 or health care provider 112. The medication event information is sent to the application server 130 for use in analysis, generation of asthma rescue event notifications, and in aggregate analyses of event data across multiple patients.

To accomplish this goal, there are a number of different ways for the sensor 120 to be constructed, and in part the construction will depend upon the construction of the medicament device itself 160. Generally, all sensors 120 will include an onboard processor, persistent memory, and the network adapter mentioned above that together function to record, store, and report medication event information to the client device 110 and/or server 130. Sensors 120 may also include a clock for recording the time and date of events.

Regarding specific sensor 120 constructions, traditional inhalers, such as mechanical dose counters, are not designed with sensors 120 in mind, and thus the sensor 120 may be constructed accordingly. Some implementations in this manner include mechanical, electrical, or optical sensors to detect movement of the device 160, priming of the device, activation of the device, inhalation by the user, etc. In contrast, modern inhalers, such as deflectable membrane dose counters, include electrical circuitry may report event information as an electrical data signal which a sensor 120 is designed to receive and interpret, for example the medicament device 160 itself may report movement, priming, and activation to the sensor 120.

More information regarding hardware and software components for the sensors 120 and medicament devices 160, as well as the interaction between them to record rescue medication events can be found in U.S. patent application Ser. No. 12/348,424, filed Jan. 1, 2009, and International Application No. PCT/US2014/039014, filed May 21, 2014, both of which are incorporated by reference herein in their entirety.

I.C. Application Server

Figure 2:
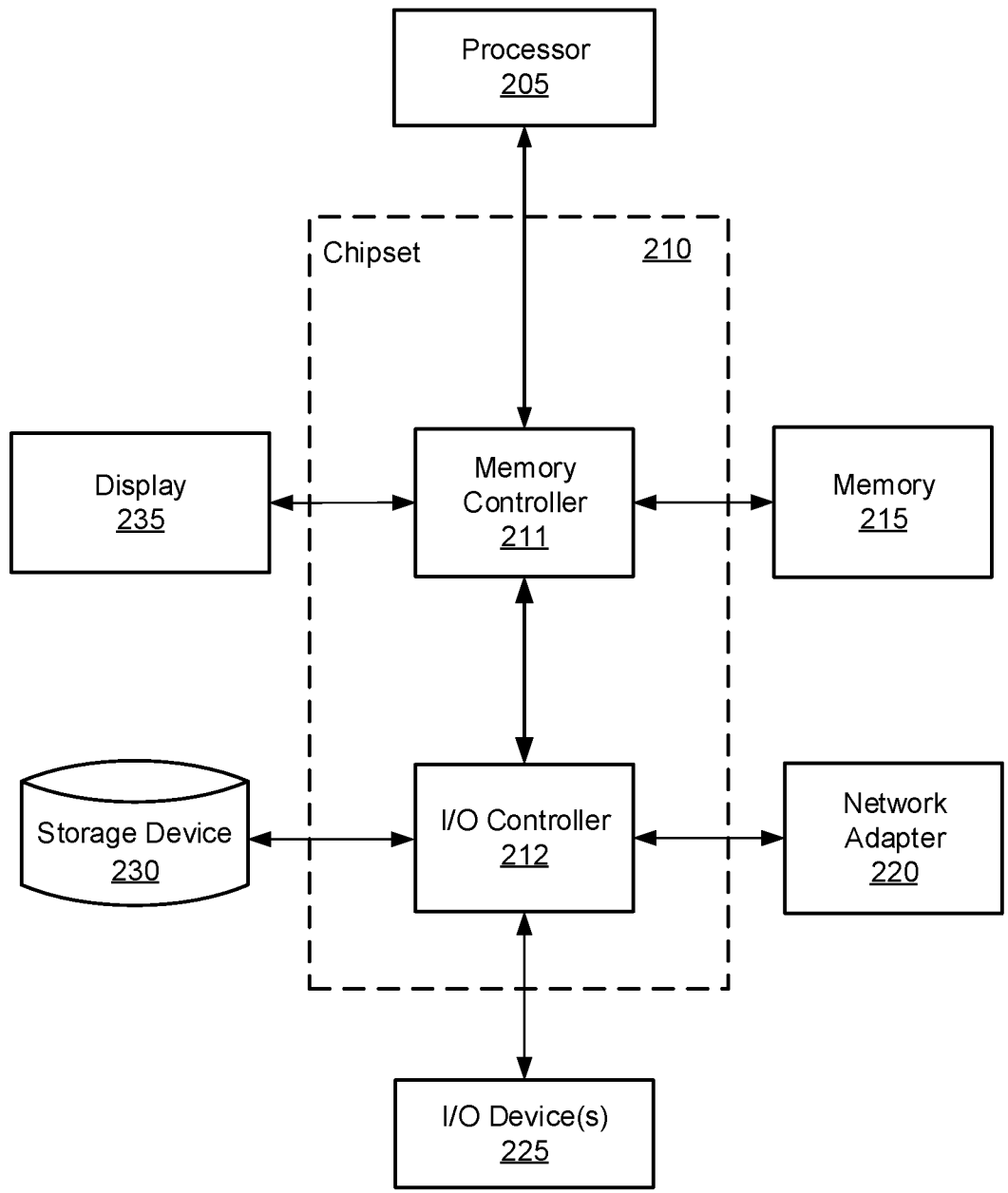
FIG. 2 is a high-level block diagram illustrating an example of a computing device used in either as a client device, application server, and/or database server, according to one embodiment.

The application server 130 is a computer or network of computers. Although a simplified example is illustrated in FIG. 2, typically the application server will be a server class system that uses powerful processors, large memory, and faster network components compared to a typical computing system used, for example, as a client device 110. The server typically has large secondary storage, for example, using a RAID (redundant array of independent disks) array and/or by establishing a relationship with an independent content delivery network (CDN) contracted to store, exchange and transmit data such as the asthma notifications contemplated above. Additionally, the computing system includes an operating system, for example, a UNIX operating system, LINUX operating system, or a WINDOWS operating system. The operating system manages the hardware and software resources of the application server 130 and also provides various services, for example, process management, input/output of data, management of peripheral devices, and so on. The operating system provides various functions for managing files stored on a device, for example, creating a new file, moving or copying files, transferring files to a remote system, and so on.

The application server 130 includes a software architecture for supporting access and use analytics system 100 by many different client devices 110 through network 150, and thus at a high level can be generally characterized as a cloud-based system. The application server 130 generally provides a platform for patients 111 and healthcare providers 112 to report data recorded by the sensors associated with their medicament devices 160 including both rescue medication and controller medication events, collaborate on asthma treatment plans, browse and obtain information relating to their condition and geographic location, and make use of a variety of other functions.

Generally, the application server 130 is designed to handle a wide variety of data. The application server 130 includes logical routines that perform a variety of functions including checking the validity of the incoming data, parsing and formatting the data if necessary, passing the processed data to a database server 140 for storage, and confirming that the database server 140 has been updated.

The application server 130 stores and manages data at least in part on a patient by patient basis. Towards this end, the application server 130 creates a patient profile for each user. The patient profile is a set of data that characterizes a patient 111 of the analytics system 100. The patient profile may include identify information about the patient such as age, gender, current rescue medication, current controller medication, notification preferences, a controller medication adherence plan, a patient's relevant medical history, and a list of non-patient users authorized to access to the patient profile. The profile may further specify a device identifier, such as a unique media access control (MAC) address identifying the one or more client devices 110 or sensors 120 authorized to submit data (such as controller and rescue medication events) for the patient.

The profile may specify which different types of notifications are provided to patients 111 and their personal healthcare providers 112, as well as the frequency with which notifications are provided. For example, a patient 111 may authorize a healthcare provider 112 to receive notifications indicating a rescue event. The patient 111 may also authorize their healthcare provider 112 be given access to their patient profile and rescue event history. If the healthcare provider 112 is provided access to the patient profile of the patient 111, the healthcare provider may specify controller adherence or rescue medication plans. Medication plans may include a prescribed number of doses per day for controller medications.

The application server 130 also creates profiles for health care providers 112. A health care provider profile may include identifying information about the health care provider 112, such as the office location, qualifications and certifications, and so on. The health care provider profile also includes information about their patient population. The provider profile may include access to all of the profiles of that provider's patients, as well as derived data from those profiles such as aggregate demographic information, rescue and controller medication event patterns, and so on. This data may be further subdivided according to any type of data stored in the patient profiles, such as by geographic area (e.g., neighborhood, city) over by time period (e.g., weekly, monthly, yearly).

The application server 130 receives rescue medication event information from the client device 110 or the sensor 120, triggering a variety of routines on the application server 130. In the example implementations described below, the data analysis module 131 executes routines to access asthma event data as well as other data including a patient's profile, analyze the data, and output the results of its analysis to both patients 111 and providers 112. This process is generally referred to as an asthma risk analysis. The asthma risk analysis may be performed at any point in time, in response to a rescue event, due to a relevant change in the patient's environment, and in response to any one of a number of triggering conditions discussed further below.

Other analyses are also possible. Specifically, any analysis that may be carried out with respect to asthma may be similar to one performed for COPD. Thus, the application server may carry out a COPD risk analysis in a manner similar to the asthma risk analysis described herein. This concept is also extended to other respiratory diseases tracked by the sensors 120 described herein.

More broadly, risk analyses (e.g., either for asthma, COPD, or other respiratory diseases) may be performed on rescue and controller medication use for multiple patients to identify based on spatial/temporal clusters (or outbreaks) of medication use based on historically significant permutations from individual, geographic, clinical, epidemiologic, demographic, or spatial or temporal baselines or predicted or expected values. Other types of analyses may include daily/weekly adherence trends, adherence changes over time, adherence comparisons to other relevant populations (e.g., all patients, patients on a particular rescue medication or controller medication or combination thereof, identification of triggers (spatial, temporal, environmental), rescue use trends over time, and rescue use comparisons to other relevant populations, and individual rescue trends versus a larger population of similar users or geographically co-located users.

Responsive to any analyses performed, the application server 130 is configured to prepare and deliver push notifications to send to patients 111, authorized healthcare providers 112, and/or other users provided access to the patient's profile. Notifications can provide details about the timing, location, and affected patient(s) 111 involved in a medication rescue event. Notifications may additionally comprise a distress or emergency signal that requests emergency assistance that are distributed to emergency assistance providers 112. Notifications may also include the results of the risk analysis performed by the data analysis module 131. More information regarding the types of notifications that may be sent and the content they may contain is further described below.

In addition to providing push notifications in response to a risk analysis, the information from the risk analysis may also be provided in other manners, such as through a website, client device 110 application, or other server-provided data platform. In one specific example, the information from a risk analysis may be provided as pull notifications, at particular time intervals. Additionally, some notifications (whether push or pull) may be triggered not in response to a risk analysis performed in response to a rescue medication event, but instead in response to a risk analysis performed in response to one of the underlying factors in the risk analysis changing (e.g., greater than a threshold change by units or by percentage), such that an updated notification is warranted. For example, if air quality conditions indicate that an increase in air pollution is occurring or is imminent, this may trigger the carrying out of risk analyses for all patients currently located in the particular geographic area where the pollution is occurring as determined, for example, based on client device 110, sensor 120, and/or medication device 160 location reporting.

Notifications are provided through the network 150 to client applications 115 in a data format specifically designed for use with the client applications, and additionally or alternatively may be provided as short message service (SMS) messages, emails, phone calls, or in other data formats communicated using other communication mediums.

I.D. Database Server

The database server 140 stores patient and provider data related data such as profiles, medication events, patient medical history (e.g., electronic medical records). Patient and provider data is encrypted for security and is at least password protected and otherwise secured to meet all Health Insurance Portability and Accountability Act (HIPAA) requirements. Any analyses (e.g., asthma risk analyses) that incorporate data from multiple patients (e.g., aggregate rescue medication event data) and are provided to users is de-identified so that personally identifying information is removed to protect patient privacy.

The database server 140 also stores non-patient data used in asthma risk analyses. This data includes regional data about a number of geographic regions such as public spaces in residential or commercial zones where a population of patents patients is physically located and may be exposed to pollutants. This data may specifically include or be processed to obtain the average patient's proximity to green space (areas including concentrated numbers of trees and plants). One example of regional data includes georeferenced weather data, such as temperature, wind patterns, humidity, the air quality index, and so on. Another example is georeferenced pollution data, including particulate counts for various pollutants at an instance of time or measured empirically. The regional data includes information about the current weather conditions for the time and place of the rescue event such as temperature, humidity, air quality index. The data may additionally include built environment data, for example land cover, impervious surface, roadways, traffic patterns, and other types of land use data. In other embodiments, the data includes social data including social determinants, demographic data, or social trend data representing a population that may be relevant to a patient or user. All of the items of data above may vary over time, and as such the data itself may be indexed by time, for example separate data points may be available by time of day (including by minute or hour), or over longer periods such as by day, week, month, or season. Although the database server 140 is illustrated in FIG. 1 as being an entity separate from the application server 130 the database server 140 may alternatively be a hardware component that is part of another server such as server 130, such that the database server 140 is implemented as one or more persistent storage devices, with the software application layer for interfacing with the stored data in the database is a part of that other server 130.

The database server 140 stores data according to defined database schemas. Typically, data storage schemas across different data sources vary significantly even when storing the same type of data including cloud application event logs and log metrics, due to implementation differences in the underlying database structure. The database server 140 may also store different types of data such as structured data, unstructured data, or semi-structured data. Data in the database server 140 may be associated with users, groups of users, and/or entities. The database server 140 provides support for database queries in a query language (e.g., SQL for relational databases, JSON NoSQL databases, etc.) for specifying instructions to manage database objects represented by the database server 140, read information from the database server 140, or write to the database server 140.

With respect to the description of FIGS. 6A-6D below, the contents of the databases described with respect to those figures may be stored in databases physically proximate to the application server 130 and separate from database server 140 as illustrated. Alternatively, those databases may be a part of database server 140, in contrast to the description of FIGS. 6A-6D illustrating them as being within data analysis module 131. This and other variations thereupon are within the scope of this description.

I.E. Network

The network 150 represents the various wired and wireless communication pathways between the client 110 devices, the sensor 120, the application server 130, and the database server 140. Network 150 uses standard Internet communications technologies and/or protocols. Thus, the network 150 can include links using technologies such as Ethernet, IEEE 802.11, integrated services digital network (ISDN), asynchronous transfer mode (ATM), etc. Similarly, the networking protocols used on the network 150 can include the transmission control protocol/Internet protocol (TCP/IP), the hypertext transport protocol (HTTP), the simple mail transfer protocol (SMTP), the file transfer protocol (FTP), etc. The data exchanged over the network 150 can be represented using technologies and/or formats including the hypertext markup language (HTML), the extensible markup language (XML), etc. In addition, all or some links can be encrypted using conventional encryption technologies such as the secure sockets layer (SSL), Secure HTTP (HTTPS) and/or virtual private networks (VPNs). In another embodiment, the entities can use custom and/or dedicated data communications technologies instead of, or in addition to, the ones described above.

II. Example Computing Devices

FIG. 2 is a high-level block diagram illustrating physical components of an example computer 200 that may be used as part of a client device 110, application server 130, and/or database server 140 from FIG. 1, according to one embodiment. Illustrated is a chipset 210 coupled to at least one processor 205. Coupled to the chipset 210 is volatile memory 215, a network adapter 220, an input/output (I/O) device(s) 225, a storage device 230 representing a non-volatile memory, and a display 235. In one embodiment, the functionality of the chipset 210 is provided by a memory controller 211 and an I/O controller 212. In another embodiment, the memory 215 is coupled directly to the processor 205 instead of the chipset 210. In some embodiments, memory 215 includes high-speed random access memory (RAM), such as DRAM, SRAM, DDR RAM or other random access solid state memory devices.

The storage device 230 is any non-transitory computer-readable storage medium, such as a hard drive, compact disk read-only memory (CD-ROM), DVD, or a solid-state memory device. The memory 215 holds instructions and data used by the processor 205. The I/O device 225 may be a touch input surface (capacitive or otherwise), a mouse, track ball, or other type of pointing device, a keyboard, or another form of input device. The display 235 displays images and other information from for the computer 200. The network adapter 220 couples the computer 200 to the network 150.

As is known in the art, a computer 200 can have different and/or other components than those shown in FIG. 2. In addition, the computer 200 can lack certain illustrated components. In one embodiment, a computer 200 acting as server 140 may lack a dedicated I/O device 225, and/or display 218. Moreover, the storage device 230 can be local and/or remote from the computer 200 (such as embodied within a storage area network (SAN)), and, in one embodiment, the storage device 230 is not a CD-ROM device or a DVD device.

Generally, the exact physical components used in a client device 110 will vary in size, power requirements, and performance from those used in the application server 130 and the database server 140. For example, client devices 110, which will often be home computers, tablet computers, laptop computers, or smart phones, will include relatively small storage capacities and processing power, but will include input devices and displays. These components are suitable for user input of data and receipt, display, and interaction with notifications provided by the application server 130. In contrast, the application server 130 may include many physically separate, locally networked computers each having a significant amount of processing power for carrying out the asthma risk analyses introduced above. In one embodiment, the processing power of the application server 130 provided by a service such as Amazon Web Services™. Also in contrast, the database server 140 may include many, physically separate computers each having a significant amount of persistent storage capacity for storing the data associated with the application server.

As is known in the art, the computer 200 is adapted to execute computer program modules for providing functionality described herein. A module can be implemented in hardware, firmware, and/or software. In one embodiment, program modules are stored on the storage device 230, loaded into the memory 215, and executed by the processor 205.

III. Dashboard

Figure 3A:
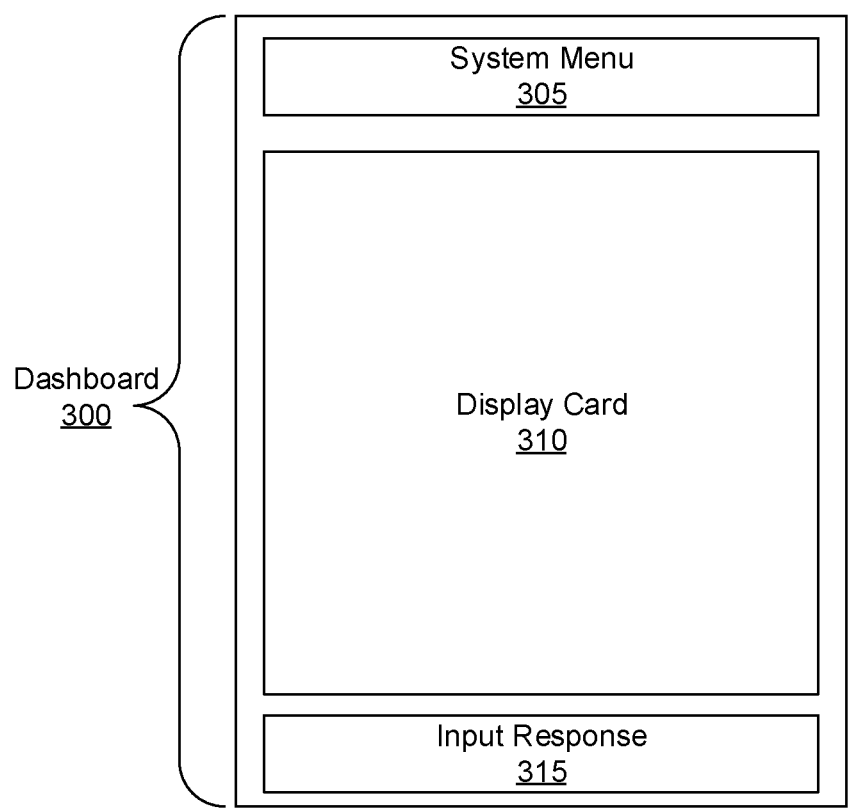
FIG. 3A shows a dashboard of a client application that allows a user to interact with an analytics system, according to one embodiment.

The dashboard, for example dashboard 300 illustrated in FIG. 3A, allows users to interact with the analytics system 100. The dashboard 300 provides a means to transfer information on a user-to-user (e.g., patient 111 to provider 112) or user-to-system/system-to-user basis. Dashboards 300 are accessed through the client application 115 on the client device 110 and provide a mechanism for both patients and healthcare providers to monitor medication rescue events, exchange personalized patient healthcare information, and receive notifications such as asthma rescue event risk notifications. Patients may communicate with other health care providers and other patients through the dashboard 300, for example, to discuss and share information about asthma, medication usage, or asthma management. The ability to share asthma healthcare information may give patients or healthcare care providers experiencing a similar issue a way to share individual perspectives.

The dashboard 300 also allows authorized health care providers 112 to access a list of patients to view, annotate, update, interact with, and export information about asthma patient and community data and statistics in various demographics or geographic segments. Using the dashboard 300, healthcare providers are able to monitor patients individually or in aggregate, to receive and provide feedback on how their associated patient populations are responding to asthma management guidance. A healthcare provider who has access to individual or multiple patients has the ability to establish notification thresholds, set parameters for the notifications, and receive notifications when patients' event history matches certain conditions (e.g. rescue event). Additionally, the dashboard 300 can receive and display regular reports of event patterns for specific demographic generated by the analytics system 100.

The dashboard 300 presents a variety of information including tabular data, graphical visualizations, and analyses to users through display "cards" 310. Display cards 310 are conformably suited to smaller displays typical of portable client devices 110, for example mobile phones or tablets, and include "bite size" pieces of information that mimic the simplistic organizational style found in baseball cards. The dashboard 300 may also include a system menu 305 that allows users to navigate through different categories of healthcare information.

Notifications provided by the application server 130 are related to the display cards 310. Generally, notifications include not only information to be presented to the user through the application 115, but also parameters for specifying which display card 310 is to be used to display the contents of the notification. Any information pushed/pulled from the application server 130 may be associated with one or more cards. For example, a notification can be pushed to the patient based on the outcome of an asthma risk analysis. The dashboard 300 will process the notification and determine which card/s to use to present the information in the notification. Continuing the example, the recipient of the notification may make a request to pull data from the application server 130. The application server 130 provides the requested data in another notification, and the dashboard 300 then determines which display card 310 to display the requested information.

To interact with information presented, some display cards 310a include a input response 315 area. For example, in the display card 310b illustrated in FIG. 3B, a patient may scroll up or down in the input response 315 area to select a controller medication used to manage asthma or select the "next" to move to an additional display card 310.

The dashboard 300 may provide a variety of different display cards 310, which may be organized into categories. An information card type includes cards that display data. Information cards may, for example, display medication rescue events, statistics, and maps including both patient data and community data. Information cards are further sub-categorized into event, trend, education, and alert display cards.

Event cards include data relating to rescue medication events, such as a list of historical medication rescue events for a specific patient, or patient rescue event data overlaid on a geographical map for a specific provider.

Figure 3B:
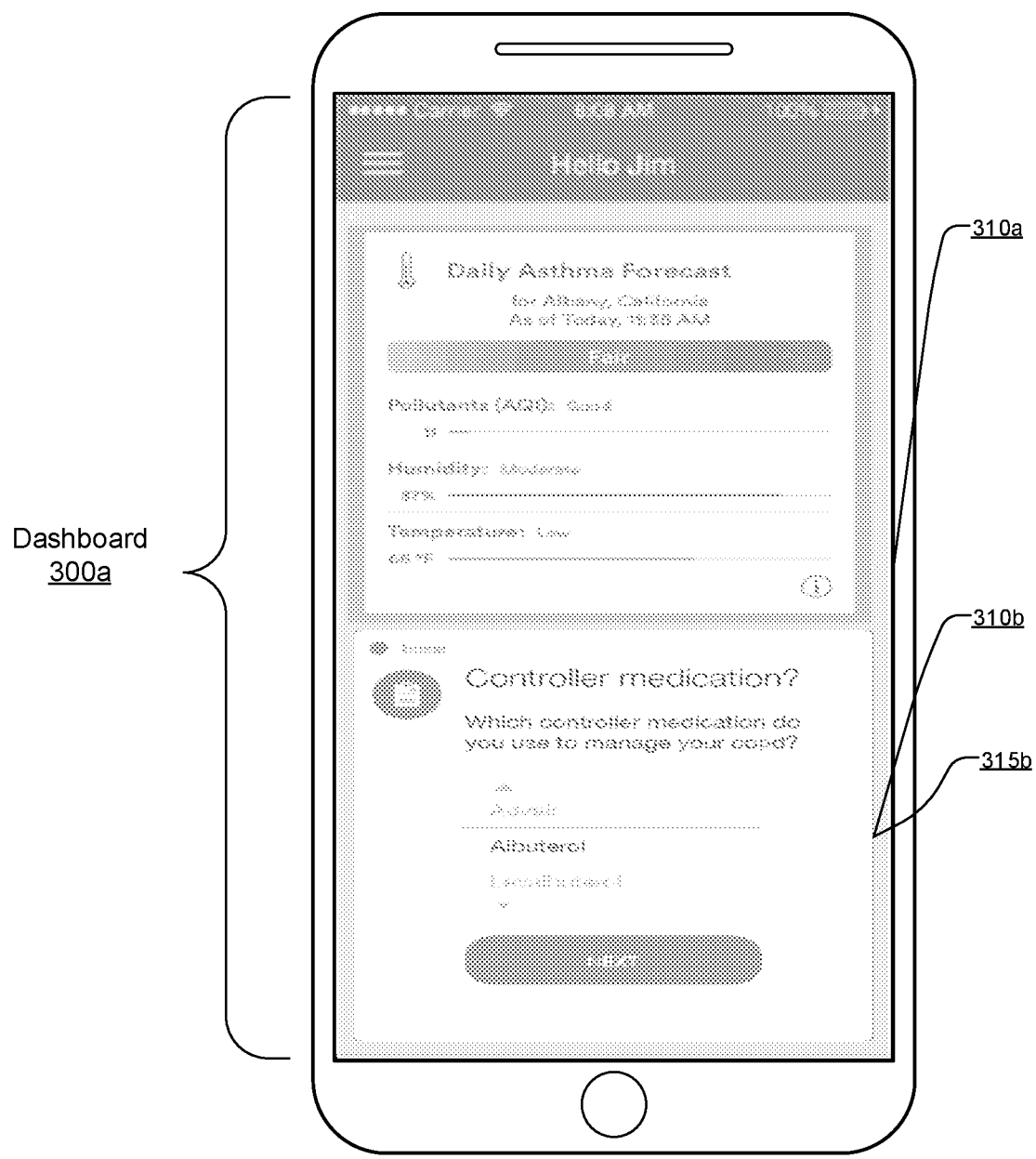
FIG. 3B shows an example card displayed within the dashboard of the client application, according to one embodiment.

FIG. 3B illustrates an example display card 310a sent by the notification module 645 (discussed below), which is sent based on the determination of a risk score by the data analysis module 131. The display card 310a highlights patient's information obtained from the input values used to determine the risk score, for example the patient's current geographical location as specified by their device 110, and environmental information. The display card 310a also includes a risk categorization based on the risk score, in this case "fair" which may represent a medium risk categorization.

Another event card may display an example medication usage report including a map of the location of a rescue usage event, environmental conditions at the location, and an input response area 315 for the recipient to add triggers for the rescue usage event. Another event trend card may display rescue device usage for the previous week including a total number of uses for the time period and a number of uses for each day.

A trend card includes statistical information presented using a graph or a chart designed for clear comprehension by the recipient. Examples of trend cards include plots of asthma rescue events over various time periods, time of day trends, days of week trends, and trigger trends.

An education card includes information meant to educate the recipient. Education cards provide general disease information and tips for patients to reduce their risk of rescue events. Some education cards may require an input response 315 to allow recipients to specify whether the information provided is relevant or interesting for use in serving future cards.

Alert cards notify users of important information including informing a recipient that they are at risk for an event and/or that data has not been received from a device over a recent time period. Other alerts may include an alert that a setting on the client device is preventing data syncing (e.g. Bluetooth is turned off) or that a patient's asthma risk score has changed.

A survey card type solicits a user response by presenting yes/no, multiple choice, or open-ended questions for the user to respond to. For example, a healthcare provider or the analytics system 100 may send a survey card with an asthma-related questionnaire to a patient 111 to determine a level of disease control for a specific patient. Additionally, a survey card may request the type of controller medication that the patient 111 uses to treat asthma symptoms. Generally, survey cards provide the application server 130 with data that may be missing from a patient's medical history or patient profile (as introduced above), and/or provide an update to potentially outdated information. One or more survey cards may be used to complete the patient enrollment process and create a patient profile for storage in database server 140. For example, when a patient 111 initially enrolls in the analytics system 100, a push notification will be triggered by the application server 130 prompting the patient 111 to create a patient profile.

Example of survey cards may include a survey question asking whether a patient has made any emergency room visits as a result of asthma rescue events, information about the patient's controller medication, how many times the patient used their rescue medication to control an event, and what their controller medication daily schedule is. Survey cards may also ask about a patient's asthma triggers, such as whether pollen is a trigger. Some survey cards may ask a patient to rate their general quality of life on 5-point Likert scale, to rate their quality of sleep, to rate their ability to be active over last 7 days, and so on. Other survey cards ask whether the patient feels better or worse than yesterday, whether the patient has had to go to emergency room or hospital in last 12 months for a rescue event and so on.

In some instances, patient behavior or sensor-reported event information that is inconsistent with existing patient information may trigger the sending of a survey card in order to resolve ambiguity as to the patient's circumstances. For example, if the patient is experiencing a greater-than-expected count of asthma events, the survey card may request information about the type of medication the patient has currently listed on their medicament device 160, in order to verify that the correct medication is being used. Another example includes if the reported information about controller medication use indicates that the patient is only using the controller medication one time per day but their adherence plan indicates they are supposed to be taking their controller medication twice per day, system 100 could send a notification asking if the patient needs to change their adherence plan.

In some instances, patient behavior or sensor-reported event information that is inconsistent with existing patient information may trigger the sending of a survey card in order to resolve ambiguity as to the patient's circumstances. For example, if the patient is experiencing a greater-than-expected count of asthma events, the survey card may request information about the type of medication the patient has currently listed on their medicament device 160, in order to verify that the correct medication is being used. As another example, if the reported information about controller medication use indicates that the patient is only using the controller medication one time per day but their adherence plan indicates they are supposed to be taking their controller medication twice per day, system 100 could send a notification asking if the patient needs to change their adherence plan.

Navigation cards represent actionable data or messages that, upon user interaction, may redirect the user to another screen or card that is part of the dashboard 300. For example, if a patient wants to share information or request specific medication plans for controller medications with a physician, a navigation card would be used to facilitate the sharing of information or enrollment in controller adherence plan. Additionally, navigation cards allow users to update information surrounding medication rescue events.

Adherence cards are designed to encourage a patient to continually use their controller medication on schedule over different periods of time. Adherence cards may indicate a "streak" or continuous run of on-time controller medication events, a better performance in aggregate even if not streak has been Additionally, a survey card may inquire as to the patient physical state in response to recording a significant number of rescue events within a threshold period of time of each other. Controller medication events may be represented as graphs to illustrate when the patient 111 did and did not take their controller medication on time during various periods during the day, as prescribed by their health care provider 112. Cards may also detail a daily schedule for controller medication and an indicator for displaying whether the scheduled dose has been taken. For example, a red "X" may indicate the scheduled dose has not been taken, but a green check mark or a different symbol may indicate that the scheduled dose has been taken.

Setup cards guide recipients in associating sensors with client devices 110. Setup cards may guide pairing a sensor to a client device 110 using Bluetooth, prompt the recipient to initiate the pairing process or prompt the user to select a sensor device for pairing, or notify the user that the sensor is paired.

In some embodiments, the dashboard may present a user interface. The user interface may illustrate a list of rescue events, responsive to the user's selection of the "View Timeline" input response area 315c. The list displays rescue usage events over a time period and includes details such as date, time, number of puffs, and location. Recipients may edit rescue usage events and/or add additional details by selecting the edit interaction response areas. Some interfaces may present an event summary for a rescue usage event to the user. The event summary may be presented to the user in response to the user selecting the edit interaction response area of the user interface. From the dashboard, the user may also view and edit a medication list, detailing information such as medication type (rescue, controller, etc.), dosage schedule, and sensors.

IV. Event-Driven Respiratory Risk Notifications

Figure 4:
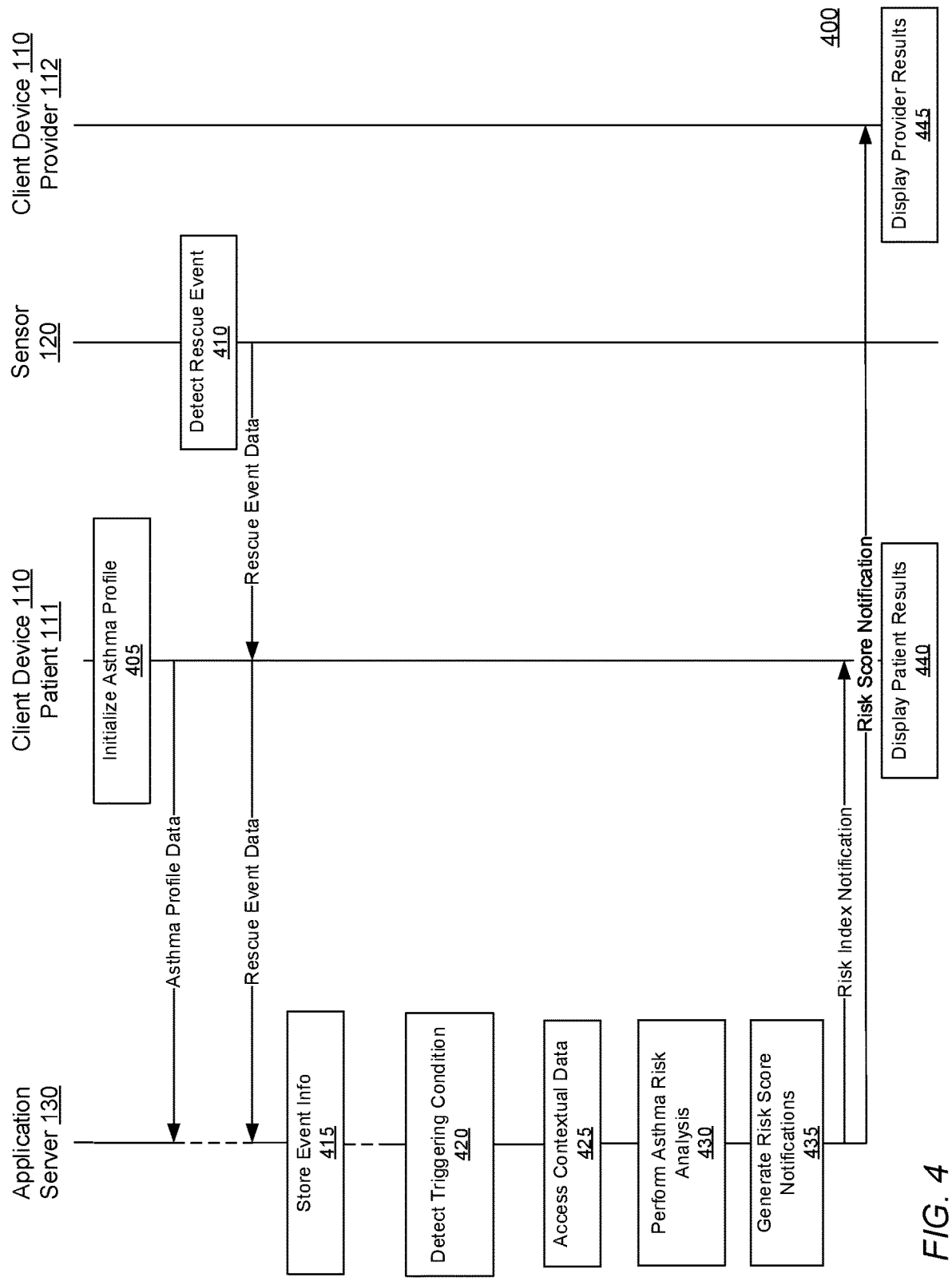
FIG. 4 is an interaction diagram for providing asthma risk-based notifications based on medicament device monitoring, according to one embodiment.

FIG. 4 shows an interaction diagram for providing asthma risk notifications based on medicament device monitoring, according to one embodiment. As introduced above, this process is equally applicable to providing risk notifications for any other type of respiratory disease, an example of which is COPD. As an initial step, a patient interfaces with the dashboard 300 to initialize 405 a patient profile. Once the patient completes their patient profile, the client device 110 transmits the patient profile for use by the application server 130 and storage by the database server 140. Once a patient's patient profile is initialized 405, the application server 130 may begin to receive rescue medications events detected by the sensor 120 associated with the patient's medicament device 160. The initializing and completing of the patient profile is only performed once during the patient's first use of the medicament device.

Upon the sensor detecting 410 a rescue usage event, the patient device 111 collects and sends the rescue event data to the application server 130, where the event information is stored 415. Although only one such instance is shown in FIG. 4, this detection and storage process is generally performed with some frequency for many patients, generally upon detection of a rescue usage event. However, this frequency may differ from the frequency with which a risk analysis is performed.

Figure 5:
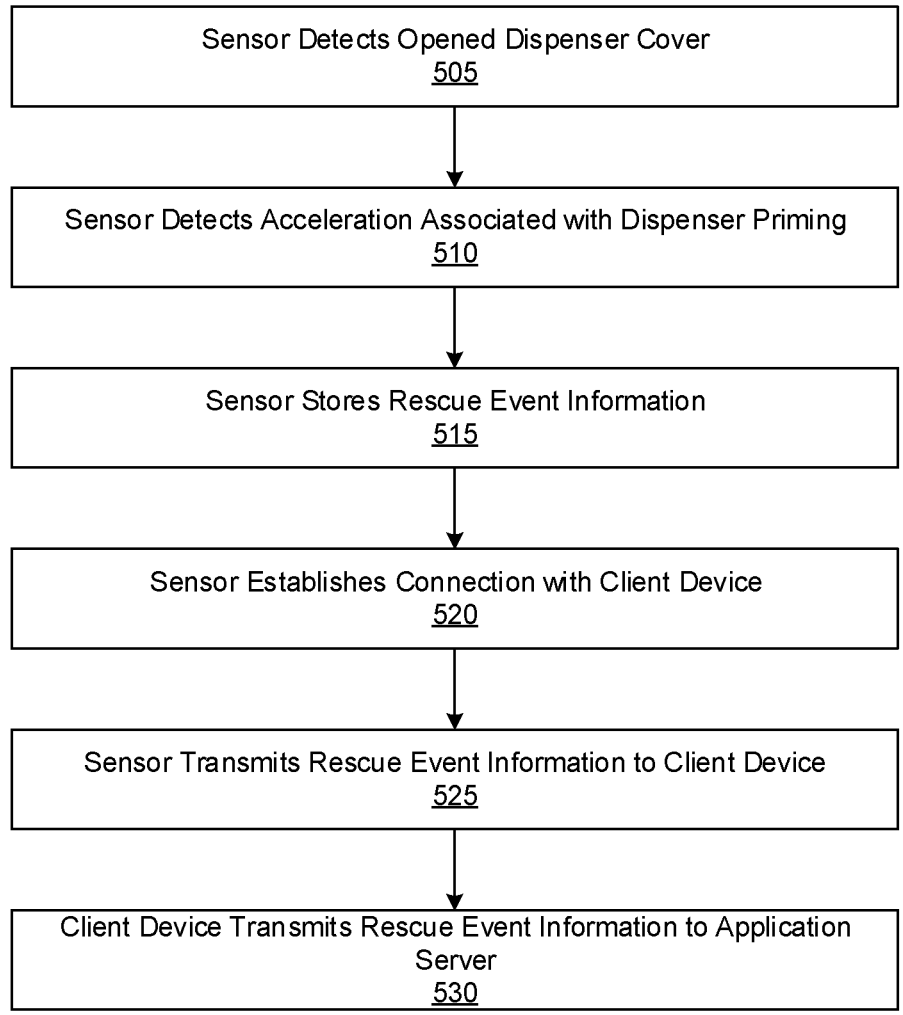
FIG. 5 is a flowchart for detecting a rescue medication event by an analytics system, according to one embodiment.

Referring now to FIG. 5, the application server 130 generally receives a rescue event anytime the patient uses their rescue medicament dispenser 160 to relieve asthma-related event symptoms. As an example of the process for capturing such an event for a particular device 160/sensor 120 combination, at the start of symptoms, the sensor 120 may detect 505 whether a medication dispenser 160 cover is opened. When the medication dispenser cover is opened, the sensor 120 may detect an acceleration 510 associated with a priming of the dispenser 160. For some types of medicament dispensers, the "priming" includes activating a mechanism to release a dose of a medication from a packaging. In other types of medicament dispensers, the "priming" includes a rapid shaking of a medication canister.

After the priming action is detected, the sensor 120 is configured to store 515 data associated with the rescue event in active memory of the sensor 120. The rescue event data may include information that describes the time and date of associated with the rescue event, the status or condition of the medicament device 160 (e.g. battery level), the number of doses of medication remaining (before or after the event), self-test results, and physiological data of a patient being treated with the medicament device 160 as measured by the sensor 120. As soon as the sensor establishes a network connection with either the client device 110 or network 150, the sensor transmits 525 any locally stored rescue event data to the client device 110 or the application server 130. If the event data was transmitted to the client device 110 first, the client device 110 then transmits 530 the rescue event data to the application server 130 as soon as the client device 110 establishes a network connection with the network 150. Depending upon the implementation, either the client device 110 or sensor 120 will add the geographic location where the event took place to the event data transmitted to the application server 130.

Returning now to FIG. 4, upon detecting 410 a rescue usage event, event data is collected and stored 415. Upon receiving and storing 415 the receiving the rescue usage event data, the application server 130 may request further information from the patient describing the rescue usage event. To obtain the information, the application server 130 generates a push notification, including the questions to be asked, to be sent to the patient's client device 110. The client device 110 may present the push notification as a survey type card 310. The patient may respond to the request by providing inputs 315 in response to the survey card 310. Alternatively, the patient 111 may elect not to respond to the request. This is permissible, any gaps in information may be obtained through later push notifications, or upon entry by provider 112 after a meeting with the patient 111. In one implementation, the failure to receive the additionally requested data in response to request does not hold up the remainder of the analysis described in steps 425-445.

The information collected as part of the event or otherwise may identify 420, information pertaining to parameters that may have played a role in triggering the event, a location of the rescue event, a label (e.g., work, home, or school) for the location, a rating to signify the personal importance of the location to the patient, and whether the use was pre-emptive (e.g., medication taken prior to exercising) in addition to any other relevant information.

In addition to requesting additional event data, the application server 130 accesses 425 stored contextual data from the database server 140. Generally, contextual data refers data other than event data, which includes but is not limited to: to atmospheric conditions, weather conditions, air quality conditions, pollen data, built environment data, demographic data, social trend data, patient data recorded from past rescue usage events, and any other considerations that are not directly detected by the medicament device at the time of the rescue usage event. By contrast, event data refers to any parameters related to the rescue event and reported by the medicament device, such as medication dosage, the time of the event, the location of the event, and relevant adherence data. Both forms of data may include temporally-current information as well as stored historical data. Accordingly, as part of obtaining the contextual data, the application server 130 also accesses historical rescue usage event data for the patient 111. This historical data can include all of the data from any past controller or rescue medication event data from the patient's history over a variety of windows of time in the past, and each historical event may include all of the same items of information as was reported 410 for this event along with any data collected upon follow up thereafter.

However, note that in the following description, such as in FIGS. 6A and 6B, in some instances contextual data 635 and historical data 620 are represented separately. The contextual data 635 refers to geographic and regional information relevant to the current event or current location of the patient's client device 110, whereas historical data 620 refers to geographic, regional, and event information from previous rescue usage events from the same or different patients.

IV.A. Asthma Prediction Model Overview

Figure 6A:
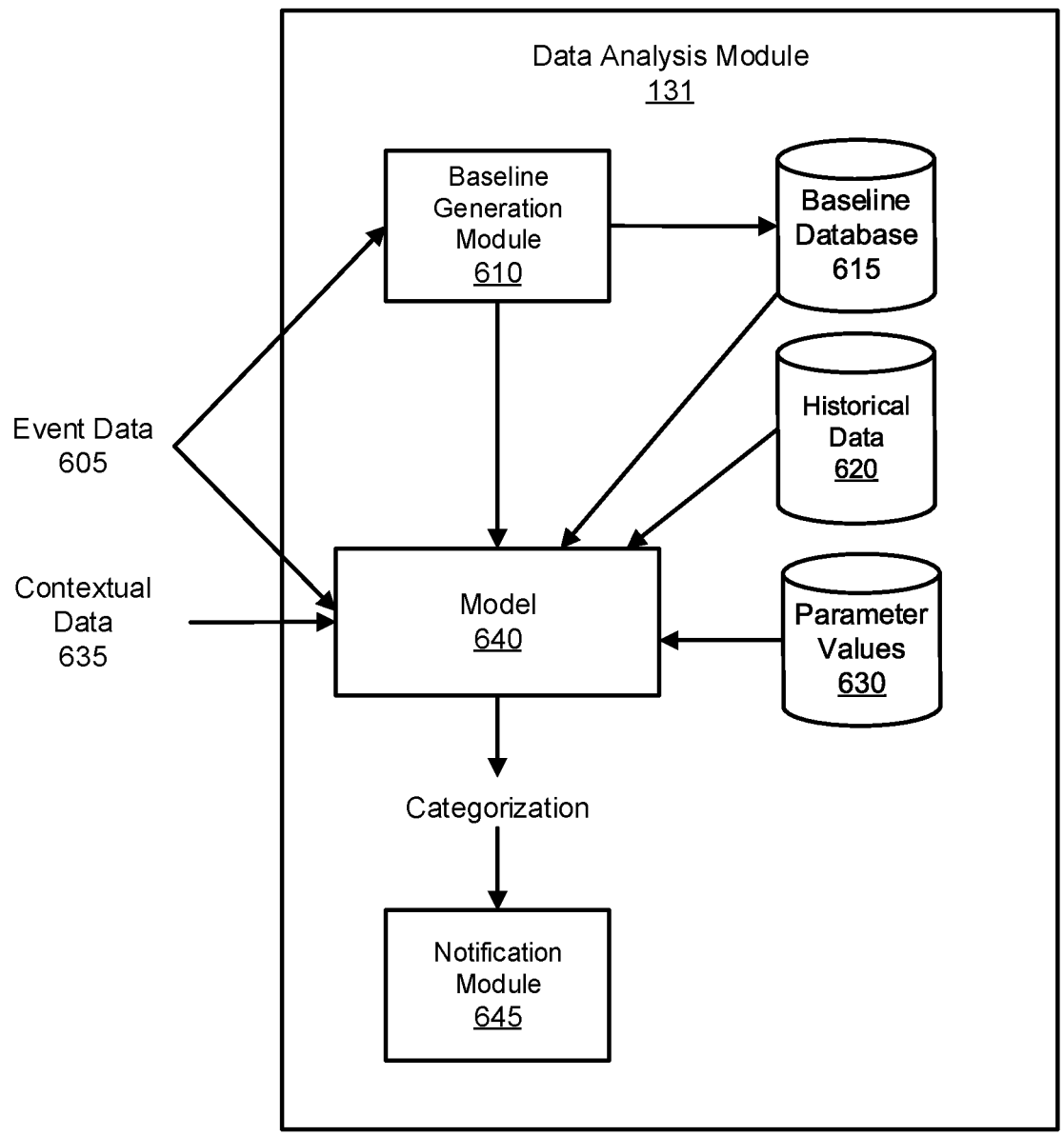
FIG. 6A is a block diagram illustrating the modules within the asthma risk score module, according to one embodiment.

FIG. 6A is a block diagram illustrating the logical components that carry out the functions of the data analysis module 131, according to one embodiment. The analytics system 100 includes, on the application server 130, a data analysis module 131 that analyses the variety of data collected by the system, introduced above and discussed further below, to perform 430 risk analyses for patients upon occurrence of a triggering condition. These risk analyses are used to generate notifications that are specifically configured to be sent to a patient in a sufficiently timely manner to hopefully avoid the occurrence of a respiratory event, such as an asthma or COPD event, which would necessitate usage of their rescue inhaler.

In order to perform a risk analysis, a model 640, such as a mathematical function or other more complex logical structure, is trained using historical event data and historical contextual data to determine a set of parameter values that are stored in advance and used as part of the risk analysis. Training is discussed with respect to FIG. 6B in Section IV.B below. Parameter values 630 describe the "weight" (or critical value or other similar quantity, depending upon the modeling technique used) that is associated with at least one of the input values. Input values refer to numerical or categorical values of the parameters of the model 640, where the input values vary between patients over time.

In one embodiment, the risk analysis is performed by inputting data on a per geographic region basis, rather than on a per user basis. In this implementation, geographic regions are segmented according to some measure, such as by 500 ft areas, latitude/longitude, census tracts, zip codes, city boundaries, states, etc. Rescue inhaler usage events 605, 620, and other contextual data 635, 620 are identified where the event temporally occurred while the sensor 120, client device 110, and/or medicament device 160 were physically located within the boundary of a geographic region. This data is then used as input values to the model's 640 function and parameters values 6430 and determine a numerical risk score for the geographic region. In some embodiments, the inputs described above are normalized based on the number of users, population density of the geographic region and/or the amount of time spent by users within the geographic region.

As above, the contextual data collected for use as the input values may be gathered automatically based on device or other third party data reporting, manually provided by a population of patients and/or provider, or otherwise obtained. In this case, risk scores generated by the model 640 characterize the likelihood that a geographic region will cause an arbitrary user (or person more generally) to experience an asthma (or other disease type) rescue usage event given event data 605 and contextual data 635. The risk score may then be used to designate a risk categorization for the geographic region that is particular to the current context for that geographic region at that moment in time, and either or both may be provided via the notification module 645 or a more general GUI interface such as dashboard 300 or through an external website.

In an alternate embodiment, the risk analysis is performed by inputting aspects of a user's rescue inhaler usage events 605, 620 and the other contextual data 635, 620 as input values to the model's 640 function and parameters values 6430 and determine a numerical risk score for the user. Generally, the contextual data collected for use as the input values may be gathered automatically based on device or other third party data reporting, manually provided by a patient and/or provider, or otherwise obtained. Risk scores are numerical values, generated by the model 640, that characterize the likelihood that a patient experiences an asthma (or other disease type) rescue usage event given event data 605 and contextual data 635. The risk score may then be used to designate a risk categorization for the user that is particular to their current context at that moment in time, and either or both may be provided to the notification module 645.

The risk analysis may be triggered by a triggering condition, which itself may be automatically scheduled, manually set, and/or occur responsive to particular event or contextual information. Examples of triggering conditions include but are not limited to: a change in an input value, for example a contextual parameter such as air pollution data, weather data, or social trends data, a result of the occurrence of a rescue event, or a conclusion of a time interval.

As part of patient or region specific risk analyses, the model 640 training process and during model use, the module 131 generates a baseline for a patient or a region, generally on a periodic basis, where the baseline is used in other functions of the risk notification process. To do this, event data 605 is received by the baseline generation module 610 and is used to generate the baseline, which is then stored in the baseline database 615 for later. This process of generating a baseline generally occurs at specified frequency regardless of the occurrence of events or triggering conditions that might otherwise trigger system action. The methodology for generating the baseline is further described below in reference to FIG. 6C-6D below.

IV.B. Model Training

Figure 6B:
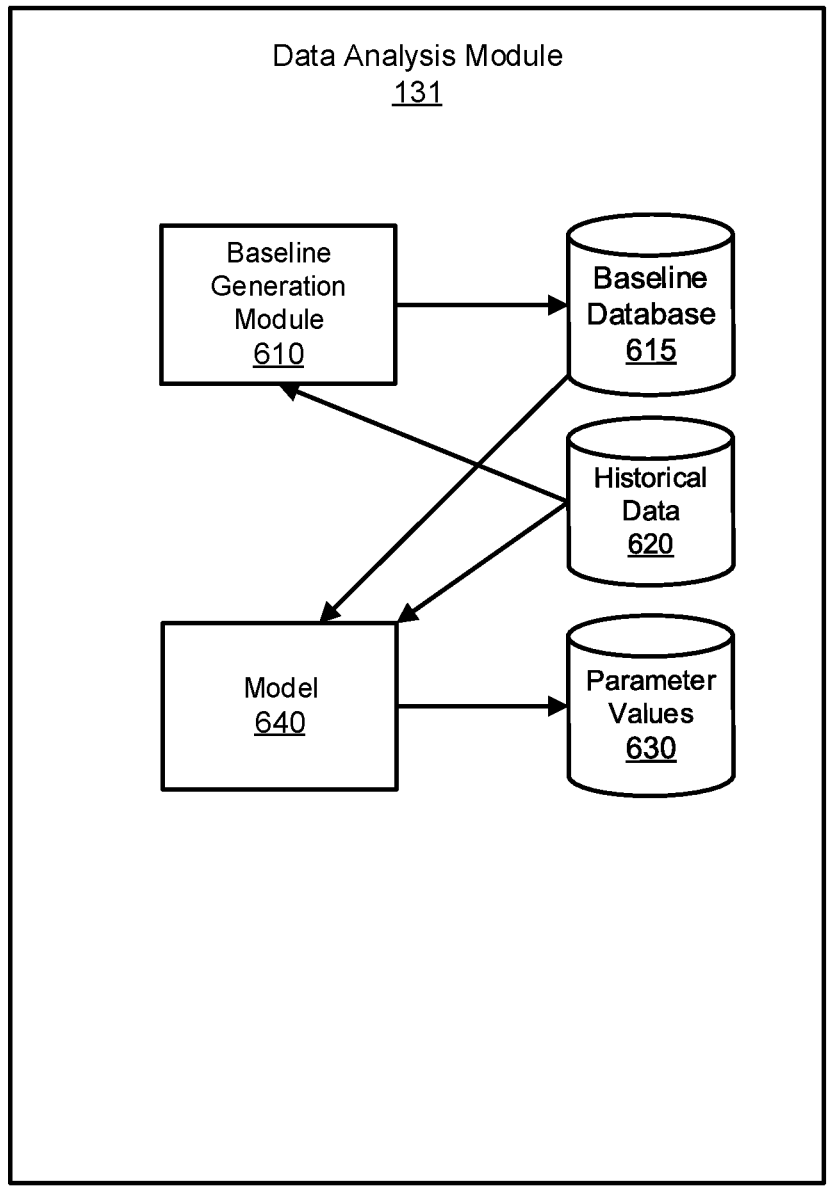
FIG. 6B is a block diagram illustrating the training modules implemented by the asthma risk score module, according to one embodiment.
Figure 6C:
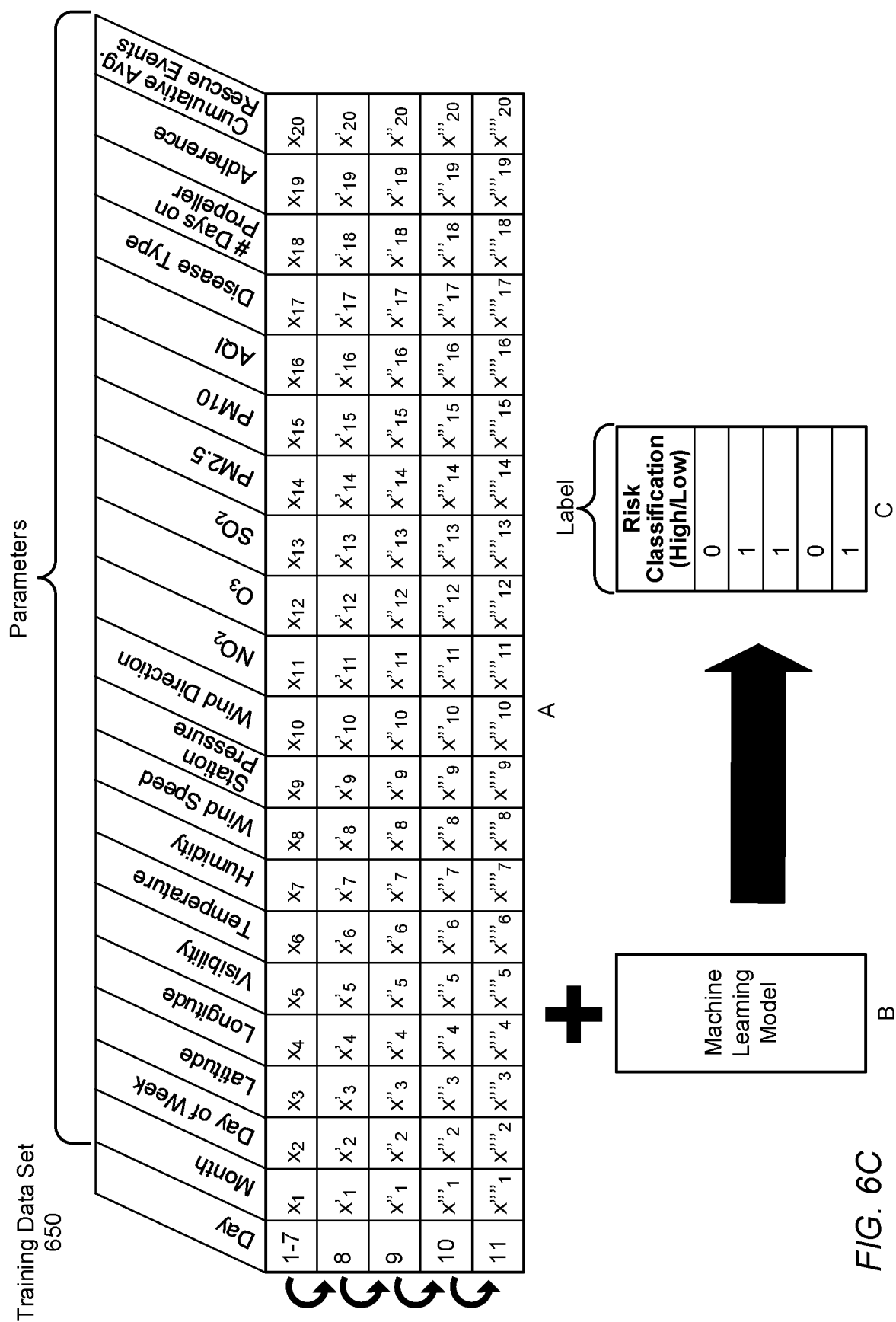
FIG. 6C is a diagram illustrating the method for training the model using the training data set, according to one embodiment.

With regard to model training and FIGS. 6B and 6C, the model is trained on labeled historical data, where historical event and historical contextual data associated with a prior day is associated with a labeled indication of whether that day was associated with high risk or low risk. This determination for the label of high or low risk is determined based on whether the events associated with the day exceed the baseline regional threshold for that day.

FIG. 6B is a block diagram illustrating a logical architecture for training the model, according to one embodiment. To create the data set used to train the model, the accessed historical data are aggregated/segmented on a per day basis, and input values for the various parameters are identified. Generally, each day's worth of information is associated with one training sample. Air quality, weather data, and other contextual data may be obtained from historical datasets specific to a region within which the patient is currently located. For example, air quality and weather data for the United States may be obtained from the National Oceanic and Atmospheric Administration (NOAA) and Environmental Protection Agency (EPA) historical data sets.

To create the label for each training sample, baseline thresholds are established for each day and the model 640 determines whether the baseline threshold is exceeded for each day based on the number of rescue usage events for that day for a person or a region. A full description regarding the determination of the baseline threshold is discussed with respect to FIG. 6D in Section IV.D below, however generally the label associated with a given training sample represents a determination of whether that day was considered to be "high risk" or "low risk".

FIG. 6C is a diagram illustrating the method for training the model using the training data set 650, according to one embodiment. The model 640 is trained by determining parameter values (e.g., associated with each parameter, not shown) that best represent the relationship between the input values (cells of the table, represented by A) of the training samples 650 (each row of the table) and the labels of those samples (C). As introduced above, the model 640 is trained using some a function (B) or another more complex logical structure. In one embodiment, the model 640 is trained using a machine learning technique, examples of which include but are not limited to linear, logistic, and other forms of regression (e.g., elastic net), decision trees (e.g., random forest, gradient boosting), support vector machines, classifiers (e.g. Naïve Bayes classifier), fuzzy matching, or deep learning techniques including sequence models (e.g., long short-term memory models). An example model 640 trained using gradient boosting is described in Section IV.E below.

Once the parameter values are known, the model 640 may be used, as discussed in FIG. 6B by accessing the parameter values and the function specified by the model, and inputting input values for the parameters to generate a risk score.

IV.C. Input Parameters

The parameters incorporated into the risk score analysis can be categorized into several groups: historical region or patient parameters, current region or patient parameters, air pollutant parameters, weather parameters, and contextual parameters. Historical and current patient parameters may be broadly categorized as simply "region parameters," or "patient parameters" based on the implementation. Air pollutants and weather variables may be more broadly categorized as simply "environmental conditions parameters." The numerical values of the parameters are factored into the generated function in the form of input values, as described above. Further, from the parameters, the parameter values of the model are derived. New parameters may be added through iterative model development.

The historical region features may include, but are not limited to: a cumulative region (or region) history of rescue events over some period of time (pr_7_rscu_sum), a cumulative count of the days that a rescue unit has been used (norm_day) in the region, the disease types (disease_asthma) within the region, a record of rescue events occurring at night within the region, a regional controller medication adherence record (pr_sun_adh), or a patient-reported outcome. Regional data may be determined based on an aggregate of data for patients within a given region. For example, the history of rescue events for the region may be a compilation of rescue events for all patients or a sub-set of patients within that region. The cumulative count of the days on which a rescue unit has been used may be an average of days during which patients within the region used the rescue unit.

Some parameters are patient specific and are not used in a geographic region risk analysis. Examples include the severity of the patient's asthma as well as their personal treatment regimen. Similarly, controller medication adherence records contain information for each patient of the population's use of their controller medication (which may also be associated with a sensor unit 160), and may also be used as parameters. Determination of this kind of feature is performed by observing instances where usage was prescribed, but not performed, instances where usages was prescribed and performed, and instances where usage was not prescribed and was performed.

Current patient features may include, but are not limited to: a current latitude (lat), longitude (lon), and location of a coordinate of the client device 110, and the current date (month, day_of_week). The current latitude and longitude are used to determine the patient's geographical location, from which information pertaining to the patient's environmental conditions can be determined. Current medication event data may also include a difference between the number of controller puffs taken versus the number prescribed to the patient, as well as a count of any rescue events that may have already occurred that day and information relevant to those events such as a count of rescue puffs taken for the rescue event. Any of the information underlying these current patient features may also be used to determine geographic region features. At least in part this information informs which events occurred in which regions, so that region specific parameters may be determined (e.g., history of rescue events over a period of time in the geographic region).

Air pollutant features may include information about concentrations (e.g., analog values), or more binary indications of presence or absence of pollutants. Examples of pollutants considered include, but are not limited to, ozone molecules (o3), nitrogen dioxide molecules (no2), sulfur dioxide molecules (so2), carbon monoxide (co), carbon dioxide (co2), particulate matter of size 2.5 micrometers or less (pm25), particulate matter of size 10 micrometers or less (pm10), pollen counts, other air pollutants, and the air quality index. In some embodiments, air pollutant parameter values are accessed periodically from data recovered by the Environmental Protection Agency and other third-party data vendors, for example on an hourly basis. Accordingly, the sensor 120 may receive a heartbeat hourly, prompting the respiratory disease risk analysis module to access updated air pollutant parameter values.

Specific weather features may include temperature (drybulbfahrenheit), humidity (relativehumidity), wind speed (windspeed), wind direction (wind_direction_cat), station pressure (stationpressure), weather type, dew point, visibility, precipitation, and thunderstorms. Similar to the description of air pollutant parameters, weather parameters may be periodically accessed from third party servers, for example the NOAA.

Contextual parameters describe social information about a patient, their living conditions, or their environment. Examples of contextual parameters include, but are not limited to socioeconomic factors, demographic factors, built environment factors, land use factors, and behavioral health factors. Demographic parameters for a region include, but are not limited to a social vulnerability index (SVI), a composition of the region broken down by race/ethnicity, age, per capita income, average household size, and education level. The SVI is a comprehensive, numerical metric developed by the Center for Disease Control and Prevention which indicates the relative vulnerability of a every census tract in the United States. The SVI ranks each tract based on 15 social factors including unemployment, minority status and disability. Accordingly, when included in region parameters 615, the parameter value assigned to the SVI is the ranking of census tract in which the geographic label is located. Built environment parameters describe measurements for a geographic region including, but not limited to, land use type, impervious surface, land surface temperature, greenness (NDVI), tree canopy, property characteristics, industrial emission sites, hazardous materials sites, traffic counts and proximity to road networks, flu activity in a region, and wildfire exposure periodically accessed from third-party servers such as the United States Geological Survey.

In some embodiments, contextual parameters also include social data capturing social trends, for example asthma searches, for a region based on trends or commonalities in patient behavior. For example, a region in which a large percentage of users perform Google searches or alternative internet-based searches related to asthma treatment is associated with a higher risk of asthma rescue usage events. As another example, a region associated with a sharp increase in inhaler rescue unit sales over a given time period may be associated with a higher risk of asthma rescue usage events. Accordingly, social trends and user behavior in a region for a given time period may be considered when determining a regional risk score for that time period.

IV.D. Threshold Determination

As introduced above, baseline risk thresholds are used both in model training and risk score calculation. The baseline generation module 610 calculates the baseline risk threshold based on the total number of usage events over a specified prior time period preceding either the current day during which the risk is being calculated (for either labeling during training or during model use), or more generally during a time period preceding the time of a current/most recent rescue usage event.

In one example, the time period is a range bounded by the current day and seven days prior, exclusive (so, excluding the current day's data from consideration), however other time periods may be used including, but not limited to, 14 days, a month, a season, annually or across multiple years. If there are not seven days' worth of data accumulated, for example due to a risk profile for a region (or a patient) having recently been created or usage events not having been tracked during this time window, the baseline may instead be calculated based on the number of days for which data is available.

In one embodiment, the baseline risk threshold is set as a fraction (percentage) of the total number of usage events for a population of patients within a region over a specified period of time. The baseline risk threshold for a region may be determined by determining an aggregate value for each regional, environmental, and contextual parameter based on a population of patients. For example, the baseline generation module 610 may determine an average value for each input parameter based on a population of patients within a region. Alternatively, the baseline generation module 610 may determine an input value based on the total number of usage events within a region.

In some implementations, the baseline determined for a population of patients may be comparable to or normalized relative to another population of patients within the same or a comparable region. The baseline risk generator 610 may group patients into populations of patients based on their location within a region (e.g., all patients within a shared region), patient parameters (e.g., patients with a similar disease type or adherence record), or a combination thereof. Accordingly, when changes in a population of patients are compared to the baseline risk threshold determined for that population, the comparison eliminates population bias because the change and the baseline risk threshold both characterize the same population of users. In some implementations, each baseline risk threshold may be normalized relative to another population of patients, for example within a neighboring geographic regions or other geographic regions spread across the country. In such embodiments, the baseline risk generator may be computed as an overall percentile relative to other geographic regions.

In another embodiment, the baseline risk generator 610 may determine the baseline risk threshold for a region based on a comparison of clinical data recorded for a region during different time periods. For example, clinical data describing treatments, rescue usage events, and other patient parameters for a region recording during a given month may be compared to a baseline risk threshold which was determined based on clinical data recorded for the same region during the same month of a previous year. In such an implementation, the comparison to the baseline risk threshold ensures that the current set of clinical data and the baseline set of clinical data are comparable in at least temporal and environmental conditions, thereby characterizing changes in patient parameters for the entire region. In alternate embodiments, clinical data for a given region during a given time period may be compared to a baseline risk threshold determined based on clinical data from recent history, or at least a comparable time period, if not specifically annual data.

Figure 6D:
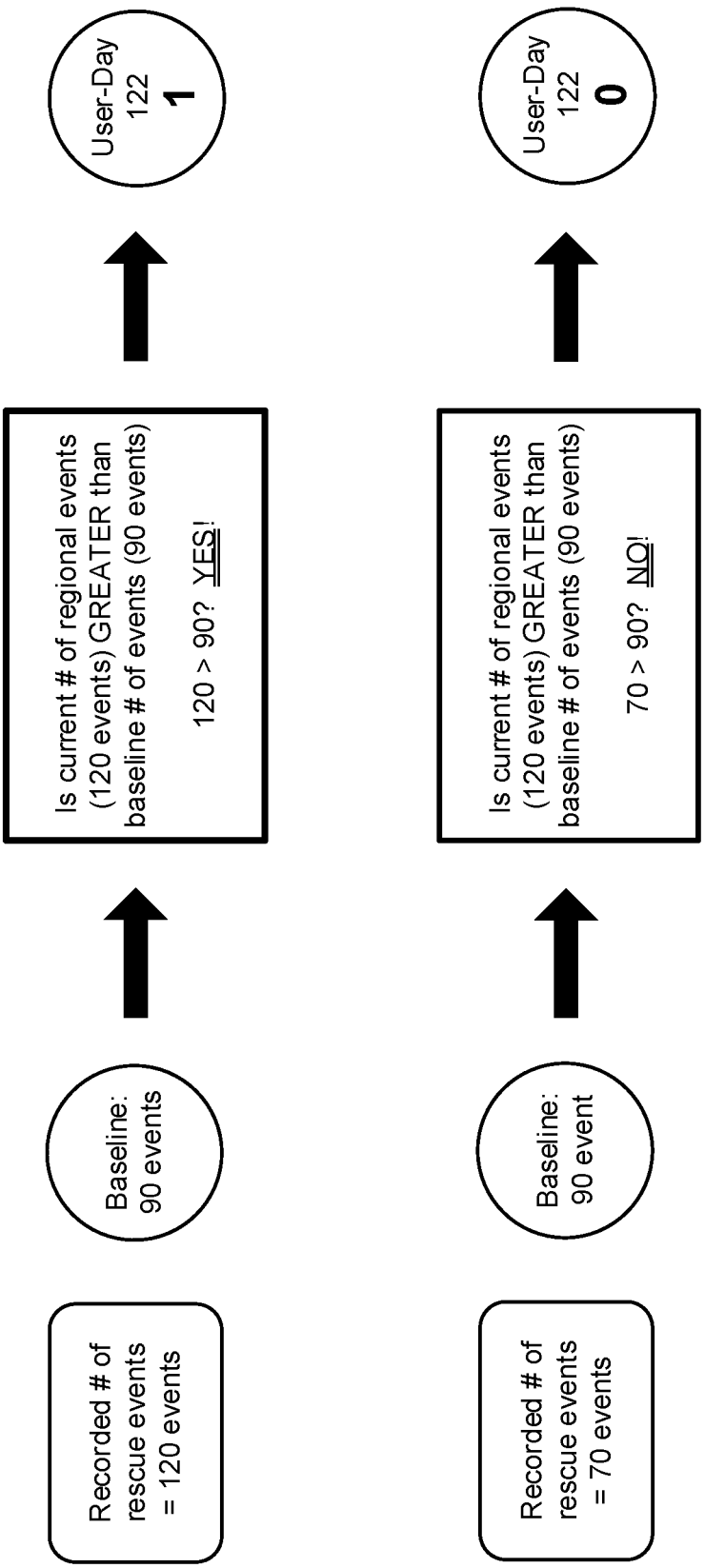
FIG. 6D is a diagram illustrating the method of establishing the threshold for risk identification, according to one embodiment.

FIG. 6D illustrates two example risk threshold determinations, and their use for determining the label for a training sample of the training data set, according to one embodiment. First, the total number of usage events for a population of users within a region during a specified period of time is summed and recorded, for example a month occurring in the year 2019. For the first and second example, this total is 120 events and 70 events, respectively. Second, the baseline risk threshold is determined as the number of rescue usage events for a similar population of users during the same period of time. In another embodiment, the baseline risk threshold is determined as the number of rescue usage events for the same population of users during a comparable period of time, for example the same month occurring the year 2018. In the illustrated embodiment, the baseline risk threshold is determined to be 90 events.

In training, samples (the events and other data related to a day's events) are labeled as "1" or "0" where 1 indicates a high risk to a patient, user, or general member of the populace and 0 indicate a low risk. As this is historical data, this "assignment" of risk is based on the assumption that the more rescue usage inhaler events occurred for a user (or in a geographic region), the worse their condition or the condition of the geographic region, suggesting some complex combination of the input values of the parameters that caused the behavior to be worse than it was on other days. Thus, in the labeling scenario it is not really a risk per se, so much as an occurrence that the model is seeking to identify in order to avoid in the future.

To assign the label, if the number of rescue inhaler usage events in a given day is greater than the threshold, here greater than 5% of the 30 events tallied over the last seven days, it is assigned a 1. Otherwise, it is assigned a 0. FIG. 6D illustrates both possible examples, in a case where 2 events are reported by the sensor 160 on a day, and in a case where 1 event is reported on the day. These definitive determinations allow the model, once trained to determine what combinations of input values and kinds of events constitute a risk event and which kinds do not. The setting of the threshold based on a fraction of the prior period's events, as opposed to a fixed number of events, allows for greater flexibility and variability in tailoring the threshold to the patient's or region's specific disease or regional state. For example, if the patient's rescue inhaler usage is elevated over a number of days, then having the threshold be dynamic in this manner allows better identification of whether the parameters are (or are not) exacerbating the patient's condition. In one embodiment, the baseline risk threshold is set to 5% rather than some higher threshold such as 14% (representing a 1 day average out of a 7 day history) to account for right tailed usage patterns with asymmetric distribution due to frequent 0's and to ensure high risk categorizations of days with usage events greater than a median day yet below the 7-day average.

IV.E. Gradient Boosted Decision Trees Example

In one embodiment, the model 640 is a gradient boosting model. Generally, gradient boosting involves the use of an ensemble of weak prediction models, typically decision trees. In the case of decision trees, each tree is a weak learner of relatively shallow depth addressing only a handful of parameters. The training mechanism of the model 640 is an iterative functional gradient descent algorithm. That is, the algorithm optimizes a cost function over the parameter space by iteratively choosing a function (weak hypothesis) that points in the negative gradient direction. Stated differently, in each iteration of training the algorithm chooses the parameters for new trees so as to minimize the error identified by the cost function from the trees and parameter values of the prior iteration.

In one specific embodiment, the XGBoost set of algorithms and framework is used as the baseline of the model 650. One example model was run with the variables of XGBoost set such that max_depth=9, min_child_weight=1, gamma=0, learning_rate=0.1, n_estimators=1000, subsample=0.8, colsample_bytree=0.8, objective=binary:logistic, scale_pos_weight, and seed=27. Additional details regarding the XGBoost algorithm can be found at http://xgboost.readthedocs.io/en/latest/python/python_api.html. Cross validation was performed on the data. For sake of convenience in the remaining description, this example is referred to as the XGBoost Example Model.

In other embodiments, the model 640 may implement different sets of algorithms and frameworks consistent with the description above.

IV.F. Prediction Model Use

Returning now to FIG. 4, the application server 130 uses the trained model performs an asthma risk analysis 430 to determine the risk that a patient will experience an asthma event in the near future. Again, these processes are equally applicable for other diseases (e.g., COPD), and can be performed for geographic regions rather than patients. This risk is embodied as a numerical score, but can also be processed into a risk categorization, such as whether the patient is within a high risk category, a medium risk category, and a low risk category. This information may be used, among other reasons, to attempt to effect a change in patient behavior to avoid the predicted event.

Referring now to FIG. 6A, the data analysis module 131 accesses input values to be able to use the model, where the input values are determined from any current rescue event data 605, historical rescue event data 635, current contextual data 635, historical contextual data 635, and the parameter values 630. The module 131 also determines or accesses a baseline risk threshold, depending upon whether a sufficiently current threshold is present in database 615. The model 640 uses these inputs to determine the risk score. As discussed above, the model 640 is trained on normalized risk values of 1 or 0, indicating whether particular prior days were or were not high "risk" for a patient or a region. The numerical risk score generated by the model 640 will similarly be a normalized value between 0 and 1 inclusive. Thus, the numerical risk score represents the model's 640 determination about whether the current input values indicate that the patient is at high or low risk. Further, recall that the 1/0 labels were based not on whether the patient had a rescue inhaler use that day per se, but whether they exceeded the dynamic threshold, which in some cases is set based on whether they exceeded some fraction of their moving-window average over a prior time period. Thus, similarly the risk score output by the model also reflects not simply whether a rescue inhaler usage event will occur, but whether a rescue usage event will occur, but instead whether based on the input values the patient is expected to exceed their own moving window average as identified by the present baseline risk threshold.

Module 131 may further categorize the risk score is categorized as a high risk, medium risk, or low risk, or some other breakdown that contextualizes the risk score. As one example, scores considered to be low risk range between 0.0 and 0.1, medium risk range between 0.1 and 0.8, and high risk range between 0.8 and 1.0.

The geographic area implementation, unlike the patient-specific implementation, is trained based on a population of patients located within a geographical region. These data may be normalized based on the number of users, population density of the geographic region and/or the amount of time spent by users within the geographic region. However, as above, the data analysis module 131 generates a risk score for a geographical region by accessing input values determined from any current contextual data 635 for the geographic region, historical contextual data 635 for the geographic region, and the parameter values 630 for the geographic region. Beyond the accessed inputs, the data analysis module 131 functions as described above to determine the risk score for the geographical region. For example, the data analysis module 131 is trained using historical contextual data 635 for the region to characterize a set of risk conditions specific to the region. The current contextual data 635 is compared with the historical data to determine a risk score for the region. In use, a user may access a provided GUI to search a specific latitude and longitude coordinate or a zip code to gain insight into the general risk of a respiratory event associated with the location.

IV.G. Rescue Event Risk Notifications

The notification module 645 generates 435 a risk score notification including any one or more of: the categorization, the risk score, potential causes for the risk score, and options that the patient can take to prevent the occurrence of another rescue usage event under these circumstances. As discussed above, the application server 130 generates 435 a risk score notification for one or more of: a geographic region, the patient 111, their healthcare provider 112, and/or any other authorized individuals.

The risk notification may include a wide variety of informational content, including the risk score, the categorization, and any of the input values from any of the parameters of the model 640.

The risk notification may also be comprised of a recommendation regarding how to prevent future rescue inhaler events based on the parameters responsible for the change in the risk categorization. For example, the recommendation may include following the adherence schedule more closely, increasing the dose or usage of a controller medication, avoiding that geographical region altogether, or limiting exposure to areas with similar environmental conditions.

Additionally, a user may be provided a geographical map with pinpoints of all of their medication rescue event locations that have occurred in the last year. As another example, a user may be provided with a geographical map including where event 410 took place, along with pinpoints of all medication rescue events that have occurred in the nearby geographical area either that day or within a threshold period of time, to indicate recent patterns in medication rescue events for that area. As another example, the healthcare provider 112 of a patient 111 may be presented with medication rescue event data from their patients 111 from that day or a recent period of time to help the provider 112 identify medication rescue event trends. As another example, a user or the public may be provided with a geographical map of where population-levels events may have occurred with a specified density.

The risk notification may also be delivered in many other situations which depending upon the implementation, may be based on triggering conditions, or may be sent to the client device according to some other mechanism. For example, if a patient's or region's current condition worsens due to changes in patient parameters (e.g., decreased patient controller medication adherence trend) or environmental condition parameters (e.g., low concentrations of ozone, greater amounts of pollutants in the air, or higher humidity) an updated risk notification is delivered to the user. Alternatively, if a patient's or region's current condition improves due to similar changes, an updated risk notification may also be delivered. Risk notifications may also be delivered at a user's request, for example due to a verbal request for local asthma conditions from a third party device (e.g., Google Home™ or Amazon Alexa™) or via other platforms.

As described above, generally risk notifications are delivered through the client device 110, however in other embodiments, in the event of improved or worsened conditions, risk notifications may be delivered as an SMS notification, an email notification, a notification from an embeddable widget with local asthma conditions, or notifications from various IFTTT applets (https://ifttt.com/).

V. Examples

V.A. Example 1

Figure 7A:
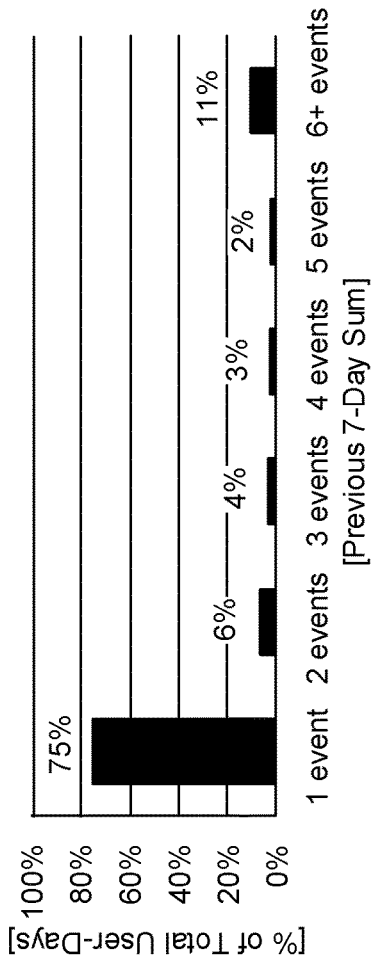
Figure 7A:
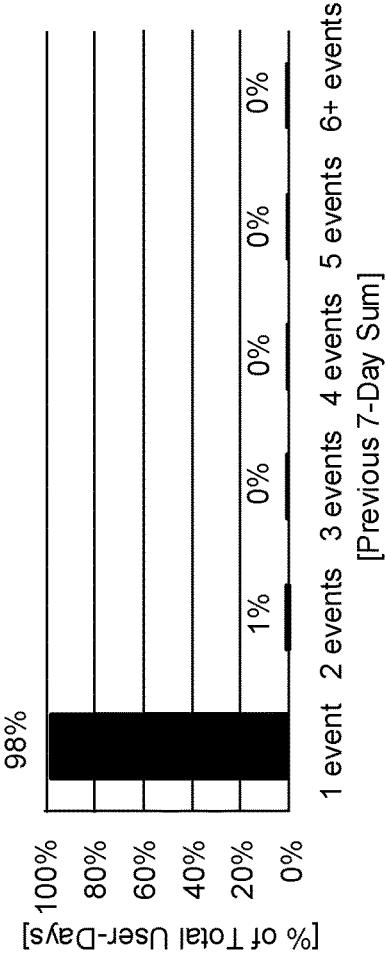

FIG. 7A characterizes the training data set, by indicating the percentage of days that were labeled as 1's and the percentage of days that labeled as 0's. Additionally, the graphs demonstrate the increase in the number of days categorized as high risk based on a baseline risk threshold that includes the 5% factor as discussed above versus a baseline risk threshold that does not. The dataset is represented per user (patient) per day, joining Propeller Health's™ patient inhaler data to air quality and weather data from the NOAA and EPA historical data sets ranging from Apr. 30, 2012 to Apr. 30, 2017. For users lacking location information, the discrepancies were filled using the most recently logged location during that 24 hour period. If no location was logged during that 24 hour period, the day's data was removed from the dataset. The total dataset comprised 5,309 users and 720,812 user days, of which 15% were categorized as high risk (or 1's). Low risk days are categorized as 0's. Of the total dataset, 5,202 users and 178,920 user days were selected for the training set. To improve model training, sub-sampling techniques have been used to balance the training set (e.g. an equal number of events labeled 0 and 1). The test set comprises 3,982 users and 35,848 users and remains unbalanced with 15% of the user days being categorized as high risk.

The data indicated that, when using the XGBoost Example Model, 98% of days having 1 event were classified as high risk, compared to the 75% of high risk days under a no-% threshold model. This significant improvement in accuracy reduces the possibility that the device fails to recognize any given high risk rescue usage event. In addition, the XGBoost Example Model now addresses the issues concerning the right tailed distribution of individual patient daily usage events, discussed above.

V.B. Example 2

FIG. 7B describes the reasoning behind setting the baseline risk threshold as percentage (e.g., 5%) of the previous time period sum of rescue usage events. A previous model (herein referred to as "V1") has categorized 26% of events as high risk (i.e., label "1") provided the most optimal combination of AUC Scores, accuracy measurements, and sensitivity and specificity readings (Sample set was based on earlier data with 30,790 patient days of data). Other similar iterations of similar models also categorized 20% of greater of patient days as high risk. This was unrealistic relative to surveyed and separately identified measurements of what percentage of most patient's days are high risk. When designing the training data set for the XGBoost Example Model, the 5% threshold was found to better represent the conventionally determined rate of high risk days (less than 5%, as indicated by FIG. 7a). To train the XGBoost Example Model, a training data was built comprising 5,202 users and 178,920 user days. To improve model training, sub-sampling techniques have been used to balance the training set (e.g. an equal number of events labeled 0 and 1).

V.C. Example 3

FIG. 7C illustrates the same performance metrics for the XGBoost Example Model.

The training and test data sets are the same data identified in FIG. 7A. These performance metrics suggest a decline in efficacy from the measurements of the V1 model, however the XGBoost Example Model addresses deficiencies of the V1 model. Part of the decrease in specificity can be attributed to a significantly larger amount of low risk days than high risk days. Only 15% of events of the test set of the XGBoost Example Model were high risk, compared to 85% of low risk events. Comparatively, the V1 test set was only 78% low risk events. Additionally, the XGBoost Example Model considers additional parameters in the performance of its risk analysis and risk categorization relative to the V1 model.

Additionally, the training data set is organized based on the geographical location of each rescue event included in the training data. Based on the recorded parameters for each rescue event of the training data set, the XGBoost Example Model predicts whether or not that geographic region is considered a high risk region (labeled as a 1) or a low risk region (labeled as a 0). Once trained, the XGBoost Example Model was able to make such predictions with an AUC score of 0.64 and at an accuracy, sensitivity, and specificity of 0.60.

V.D. Example 4

Figure 7D:
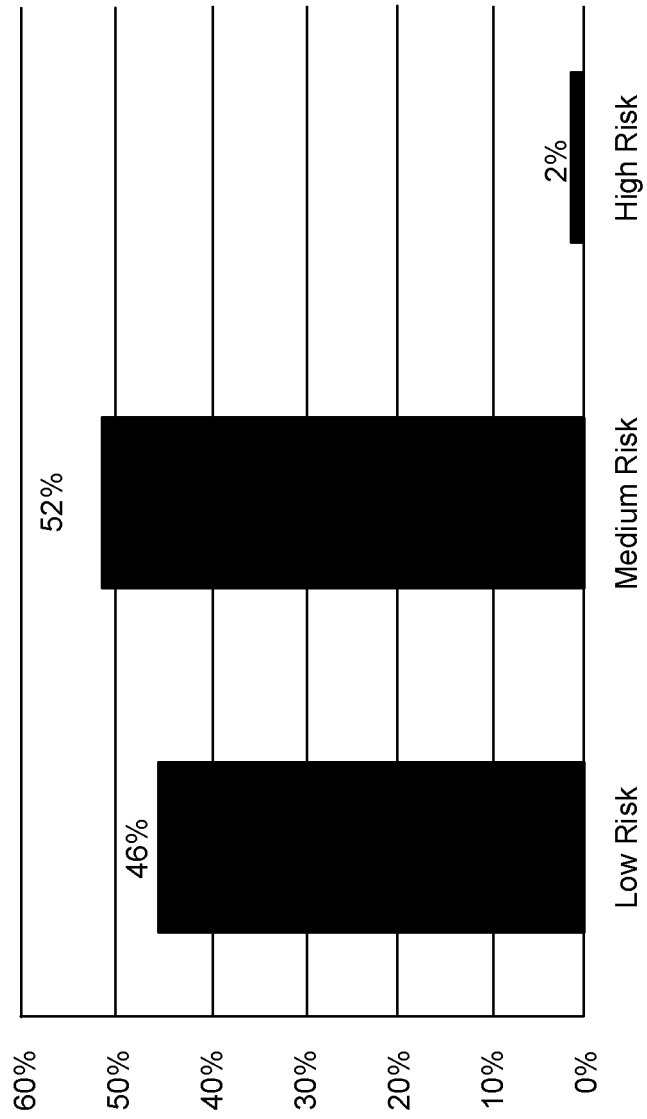
Figure 7E:
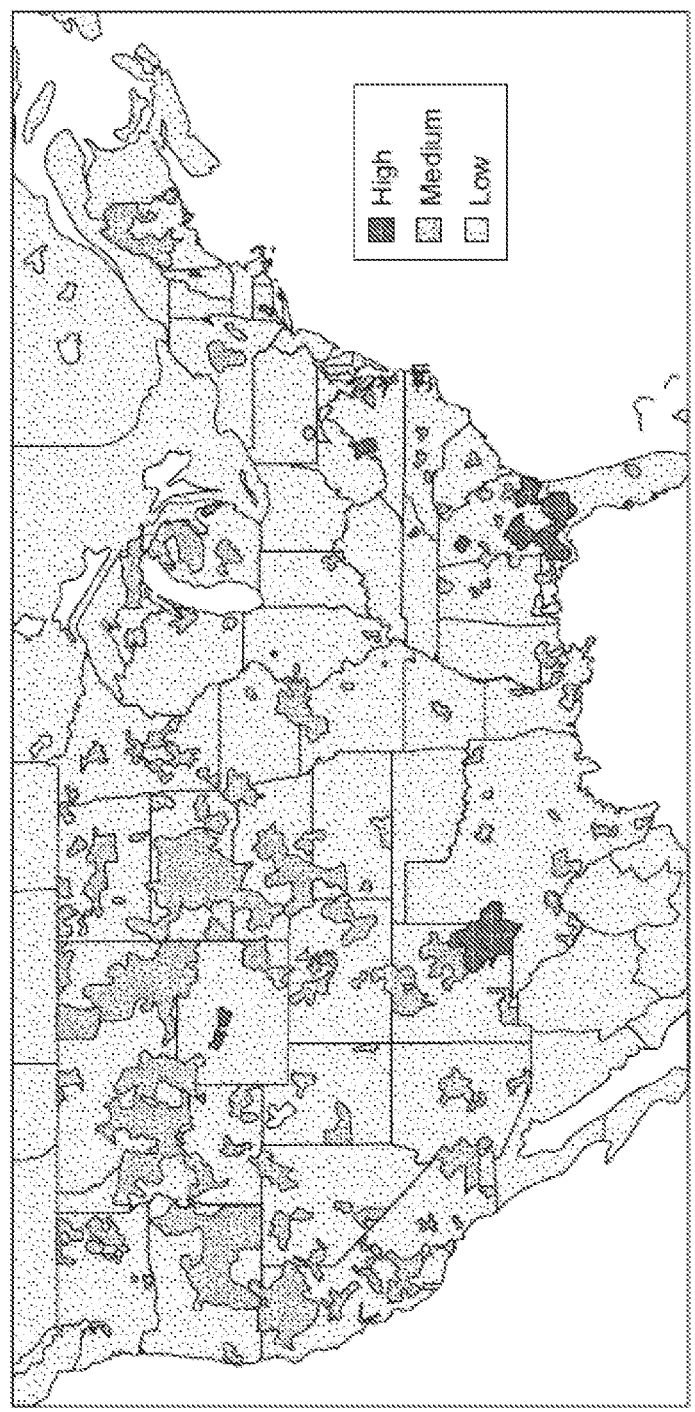
Figure 7F:
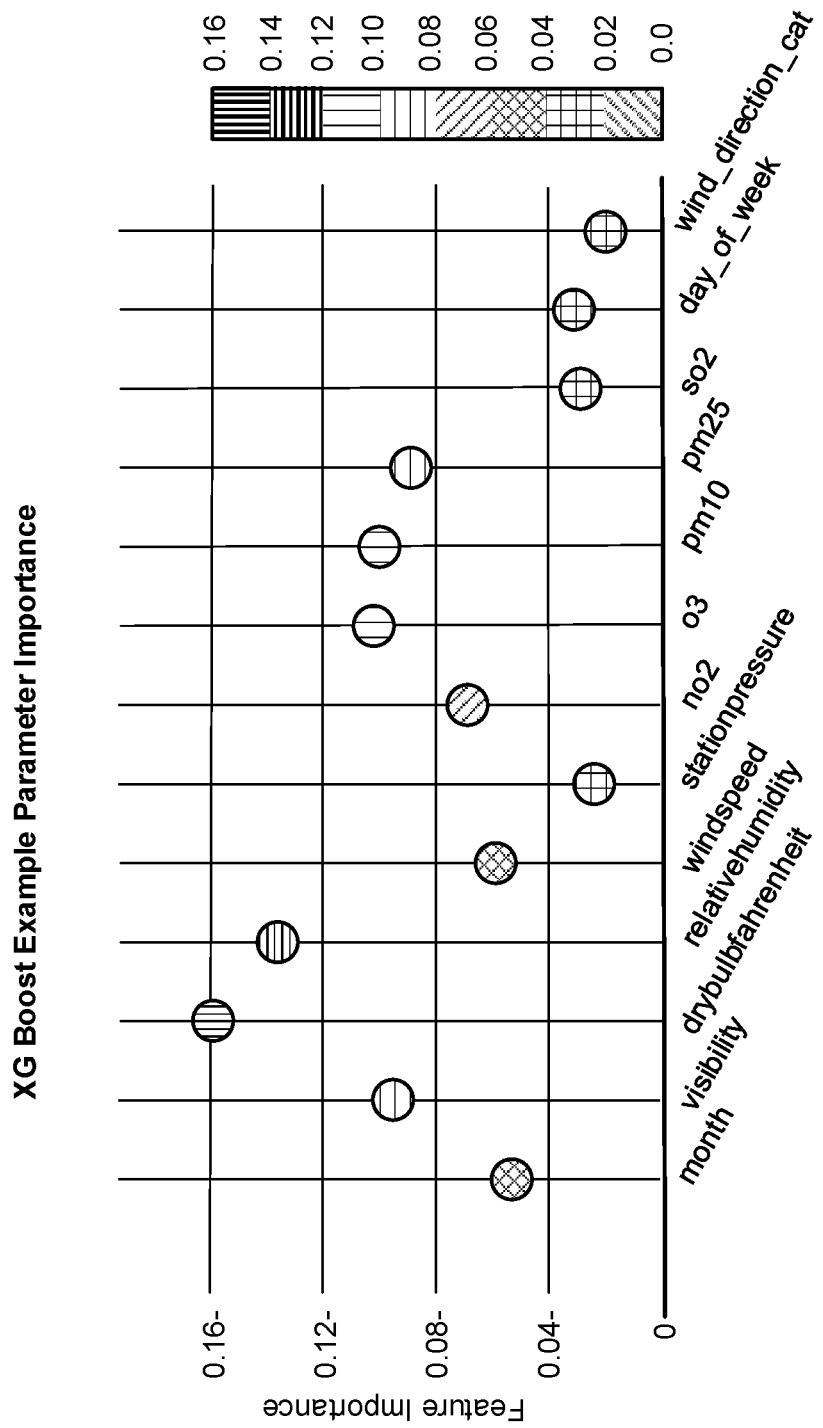

FIG. 7D displays a distribution of regions from the test set categorized as high risk, medium risk, and low risk by the XGBoost Example Model. Regions considered medium risk make up the majority of the test set at 52%, followed by regions considered low risk at 46%, and regions considered high risk at 2%. This risk category distribution is broadly consistent with the categorizations generated by the V1 model, wherein low and medium risk predictions far outnumbered the high risk predictions. Specifically, in the V1 model, low risk predictions accounted for 49% of the test set, medium risk predictions accounted for 32%, and high risk predictions accounted for 20%. FIG. 7E displays a graphic representation of the United States with a distribution of risk scores over multiple geographic regions. The majority of regions in the United States are categorized as low risk, followed by a smaller amount of region categorized as medium risk, with the fewest amount of regions categorized as high risk.

V.E. Example 5

FIG. 7D diagrams a number of parameters of the XGBoost Example Model and assigns each parameter an importance score representing the importance of the parameter in the risk analysis determination. Determining the importance of the various parameters is completed during the training of the model, wherein the model determines the parameter values to associate with the parameters. As such, the training data set is consistent with the characterizations described in reference to FIG. 7A-7B. For this example, based on the identified model parameters and test data, the most important parameter is the dry bulb temperature, with a score of 0.16 and the least important parameter is the wind direction, with a score of 0.023. The most important air pollutant parameters are the concentration of ozone molecules and concentration of particulate matter, 1 micrometer or less, with scores of 0.1095.

VI. Benefits

The asthma rescue event risk notifications provided to patients 111, providers 112, and users more generally convey many benefits. Patients are informed of their risk of an asthma rescue event in real time or near real time (on the order of seconds to minutes), and can take action to prevent that occurrence, for example by improving their adherence to their controller medication, staying away from geographic areas with adverse conditions (e.g., air pollution concentrations), adding or altering their prescribed medication regimen (such as an adjustment of dosage or the introduction of antibiotics or systemic corticosteroids), or scheduling an appointment with their doctor to address their recent spike in use of rescue medication which in turn would reduce the frequency of emergency room and hospital visits for the patient. Because the event data is automatically reported to the application server 130 without the need for patient input, the accuracy and quality of the event data is improved relative to manually-collected data by a health care provider 112 or other entity, and thus the accuracy of the conclusion for the risk of asthma rescue events is also improved.

Additionally, follow up notifications provided by the application server 130 including reports of nearby rescue medication events by other patients can provide patients with additional information about others who are suffering from similar issues and provide regional information relevant for the patient's decision-making. Follow up notifications can further encourage the user regarding progress on taking their adherence medication. Ideally such notifications will prevent the occurrence of asthma rescue events, thus preventing patient harm as well as hospital visits and their associated costs.

Health care providers informed of the risk of one or more of their patients' risk of asthma rescue events can similarly track the progress of their patients, and use the information to update their treatment regimen for each patient, schedule appointments with patients, and so on. For patients at high risk of asthma rescue events, the notification may be a call to action for the health care provider to communicate with the patient and encourage them to seek medical treatment. Follow up notifications may provide information about regional effects (e.g., pollution), patient controller medication adherence, etc.

Information describing a risk analysis for a geographic region allows patients suffering from respiratory diseases to make informed lifestyle choices regarding different geographical regions. For example, when searching for real estate, the ability to eliminate geographic regions with a high risk of respiratory event allows patients to make informed decisions to improve their health. Similarly, when traveling, prior knowledge of a risk for region allows patients to prepare the necessary precautions. As a result, a risk analysis for a geographic regions provides patients with anticipatory knowledge necessary for them to reduce their risk of respiratory events wherever their location may be.

VII. Additional Considerations

Although the discussion above focuses on asthma, all systems and processes described herein are equally applicable to chronic obstructive pulmonary disease (COPD) and chronic respiratory disease (CRD) generally, and consequently can also be used to assist in treatment of COPD and CRD, as well as asthma.

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A method comprising:
accessing a set of historical rescue inhaler usage events recorded for a population of patients within a region, each event of the set of historical rescue inhaler usage events previously received from one of: a client device, the rescue inhaler unit, or a medicament device sensor removably attached to the rescue inhaler unit and configured to monitor medicament usage of the rescue inhaler unit, wherein a historical rescue inhaler usage event is recorded when the rescue inhaler unit dispenses a rescue medication to one of the patients within the region;
determining a region-specific baseline risk threshold based on a value representing a percentage of the set of historical rescue inhaler usage events recorded for the population of patients within the region over a time period;
responsive to a triggering condition,
accessing a set of input values;
inputting the set of input values, and the region-specific baseline risk threshold into a machine-learned model to determine a risk score for the region, the machine-learned model trained using a training dataset to determine a set of parameter values, the training dataset comprising input values recorded during a historical rescue inhaler usage event in a region and labeled with a risk score determined for the region during the prior rescue inhaler usage event and the set of parameter values representing a relationship between each input value and the risk score determined for the region; and
generating, for presentation on a computing device of each patient in the region, a notification comprising an updated adherence schedule for dispensing rescue medication to the patient based on the risk score.

2. The method of claim 1, further comprising:
receiving the set of historical rescue inhaler usage events from the client device, the medicament device sensor, or the rescue inhaler unit.

3. The method of claim 1, wherein the region-specific baseline risk threshold is determined with respect to a prior time period, the prior time period including events from a window of time preceding a current time.

4. The method of claim 3, wherein the region-specific baseline risk threshold is determined as a percentage of a sum of historical rescue inhaler usage events within the prior time period.

5. The method of claim 1, wherein the region-specific baseline risk threshold is periodically determined.

6. The method of claim 1, wherein the triggering condition includes a threshold change in a physical location of the client device.

7. The method of claim 1, wherein the triggering condition includes a periodic conclusion of a time interval.

8. The method of claim 1, wherein the triggering condition includes a threshold change in an input value of at least one of a plurality of parameters.

9. The method of claim 1, wherein the set of parameter values are determined using a boosted gradient model.

10. The method of claim 1, wherein the risk score is a numerical value representing a likelihood that a user in the region on a current day will experience a number of rescue inhaler usage events exceeding the threshold that day.

11. The method of claim 1, wherein the set of parameters include at least one contextual data parameter.

12. The method of claim 1, wherein the set of parameters include one or more of the following:
at least one current region parameter, further comprising:
a current latitude and longitude coordinate of the client devices of the plurality;
a geographical region;
a current date;
a difference in number of controller puffs taken by the patient and prescribed for the patient; and
a count of rescue puffs taken for a rescue inhaler usage event.

13. The method of claim 1, wherein the set of parameters include one or more of the following:
at least one air pollutant parameter, further comprising:
a concentration of ozone molecules ($O_3$);
a concentration of nitrogen dioxide molecules ($NO_2$);
a concentration of sulfur dioxide molecules ($SO_2$);
a concentration of carbon monoxide molecules (CO);
a concentration of carbon dioxide molecules ($CO_2$);
particulate matter, 2.5 micrometers or less ($PM_{2.5}$);
particulate matter, 1 micrometer or less ($PM_{1.0}$); and
air quality index (AQI).

14. The method of claim 1, wherein the set of parameters include one or more of the following:
at least one weather parameter, further comprising:
temperature;
humidity;
wind speed;
wind direction;
station pressure;
precipitation;
thunderstorms; and
visibility.

15. The method of claim 1, wherein the set of parameters include:
temperature,
relative humidity,
wind speed,
nitrogen dioxide ($NO_2$);
sulfur dioxide ($SO_2$);
particular matter 2.5 micrometers or less ($PM_{2.5}$); and
particulate matter 1 micrometers or less ($PM_{1.0}$).

16. The method of claim 1, wherein the risk notification is presented at a first time that is different from a second time when the region-specific baseline risk threshold is determined.

17. The method of claim 1, wherein the notification comprises informational content regarding the triggering condition.

18. The method of claim 1, wherein the notification comprises informational content regarding at least one of:
the triggering event;
the region-specific baseline risk threshold; and
a risk categorization based on the regional risk score.

19. The method of claim 1, wherein the risk notification further comprises informational content regarding an inhaler rescue usage event, wherein the informational content further comprises a subset of parameters responsible for a change in risk categorization compared to a previous time period.

20. The method of claim 19, wherein the risk notification further comprises informational content regarding the rescue inhaler usage event, wherein the informational content further comprises a recommendation regarding how to prevent future rescue inhaler events and is based on the subset of parameters responsible for the change in risk categorization.

21. A non-transitory computer readable storage medium comprising computer program instructions that when executed by a computer processor cause the processor to:
   access a set of historical rescue inhaler usage events recorded for a population of patients within a region, each event of the set of historical rescue inhaler usage events previously received from one of: a client device, the rescue inhaler unit, or a medicament device sensor removably attached to the rescue inhaler unit and configured to monitor medicament usage of the rescue inhaler unit, wherein a historical rescue inhaler usage event is recorded when the rescue inhaler unit dispenses a rescue medication to one of the patients within the region;
   determine a region-specific baseline risk threshold based on a value representing a percentage of the set of historical rescue inhaler usage events recorded for the population of patients within the region over a period of time;
   responsive to a triggering condition,
      access a set of input values;
      input the set of input values, and the region-specific baseline risk threshold into a machine-learned model to determine a risk score for the region, the machine-learned model trained using a training dataset to determine a set of parameter values, the training dataset comprising input values recorded during a historical rescue inhaler usage event in a region and labeled with a risk score determined for the region during the prior rescue inhaler usage event and the set of parameter values representing a relationship between each input value and the risk score determined for the region; and
   generate, for presentation on a computing device of each patient in the region, a notification comprising an updated adherence schedule for dispensing rescue medication to the patient based on the risk score.

\* \* \* \* \*